(12) United States Patent
Steinberg

(10) Patent No.: US 7,780,740 B2
(45) Date of Patent: Aug. 24, 2010

(54) METHODS, SYSTEMS, AND APPARATUS FOR IMPLANTING PROSTHETIC DEVICES INTO CARTILAGE

(75) Inventor: Amiram Steinberg, Avihail (IL)

(73) Assignee: Active Implants Corporation, Memphis, TN (US)

( * ) Notice: Subject to any disclaimer, the term of this patent is extended or adjusted under 35 U.S.C. 154(b) by 301 days.

(21) Appl. No.: 12/124,709

(22) Filed: May 21, 2008

(65) Prior Publication Data

US 2008/0294266 A1 Nov. 27, 2008

Related U.S. Application Data

(60) Provisional application No. 60/939,323, filed on May 21, 2007.

(51) Int. Cl.
*A61F 2/32* (2006.01)
(52) U.S. Cl. .................................. 623/22.21
(58) Field of Classification Search .... 623/22.21–23.15
See application file for complete search history.

(56) References Cited

U.S. PATENT DOCUMENTS

| | | | |
|---|---|---|---|
| 3,982,281 A * | 9/1976 | Giliberty | 623/22.24 |
| 4,828,565 A * | 5/1989 | Duthoit et al. | 623/22.3 |
| 4,834,759 A * | 5/1989 | Spotorno et al. | 623/22.3 |
| 4,865,604 A * | 9/1989 | Rogozinski | 623/23.42 |
| 4,997,447 A * | 3/1991 | Shelley | 623/22.31 |
| 5,080,677 A * | 1/1992 | Shelley | 623/22.24 |
| 5,080,678 A * | 1/1992 | Spotorno et al. | 623/22.14 |
| 5,108,404 A * | 4/1992 | Scholten et al. | 606/94 |
| 5,108,446 A * | 4/1992 | Wagner et al. | 623/22.28 |
| 5,108,448 A * | 4/1992 | Gautier | 623/22.26 |
| 5,755,799 A * | 5/1998 | Oehy et al. | 623/18.11 |
| 5,766,260 A * | 6/1998 | Whiteside | 623/22.27 |
| 5,827,289 A * | 10/1998 | Reiley et al. | 606/86 R |
| 5,879,397 A * | 3/1999 | Kalberer et al. | 623/22.25 |
| 5,879,398 A * | 3/1999 | Swarts et al. | 623/22.21 |
| 5,879,402 A * | 3/1999 | Lawes et al. | 128/898 |
| 5,879,404 A * | 3/1999 | Bateman et al. | 623/22.21 |
| 5,904,720 A * | 5/1999 | Farrar et al. | 623/22.15 |
| 5,913,858 A * | 6/1999 | Calandruccio et al. | 606/79 |
| 5,919,236 A * | 7/1999 | Pfaff et al. | 623/18.11 |
| 5,928,285 A * | 7/1999 | Bigliani et al. | 623/19.13 |
| 5,931,870 A * | 8/1999 | Cuckler et al. | 623/22.21 |
| 5,935,175 A * | 8/1999 | Ostiguy et al. | 623/22.28 |
| 5,938,702 A * | 8/1999 | Lopez et al. | 623/22.38 |
| 5,944,757 A * | 8/1999 | Grammont | 128/898 |
| 5,997,582 A * | 12/1999 | Weiss | 606/89 |
| 6,110,211 A * | 8/2000 | Weiss | 623/23.11 |
| 6,136,038 A * | 10/2000 | Raab | 623/23.37 |

(Continued)

*Primary Examiner*—Alvin J. Stewart
(74) *Attorney, Agent, or Firm*—Haynes and Boone LLP

(57) ABSTRACT

A method of implanting a prosthetic acetabular cup into a patient is disclosed. The method comprises gaining access to an acetabulum of the patient, where the acetabulum includes an inner portion formed of bone and an outer portion formed of articular cartilage. The method also comprises creating a recess within the articular cartilage of the outer portion of the acetabulum without removing any portion of bone from the inner portion of the acetabulum. The recess is shaped to mate with a snap-fit structure of the prosthetic acetabular cup. Finally, the method comprises securely engaging the prosthetic acetabular cup with the acetabulum by snap-fitting the snap-fit structure of the prosthetic acetabular cup with the recess in the articular cartilage of the outer portion of the acetabulum.

20 Claims, 16 Drawing Sheets

U.S. PATENT DOCUMENTS

| | | | |
|---|---|---|---|
| 6,231,611 B1* | 5/2001 | Mosseri | 623/22.12 |
| 6,264,698 B1* | 7/2001 | Lawes et al. | 623/22.12 |
| 6,663,647 B2* | 12/2003 | Reiley et al. | 606/192 |
| 6,682,567 B1* | 1/2004 | Schroeder | 623/22.24 |
| 6,755,865 B2* | 6/2004 | Tarabishy | 623/22.12 |
| 6,811,569 B1* | 11/2004 | Afriat et al. | 623/22.32 |
| 6,827,720 B2* | 12/2004 | Leali | 606/96 |
| 6,896,703 B2* | 5/2005 | Barbieri et al. | 623/22.3 |
| 7,445,595 B2* | 11/2008 | Brannon | 600/114 |
| 7,553,332 B2* | 6/2009 | Bacon | 623/22.3 |
| 7,572,295 B2* | 8/2009 | Steinberg | 623/22.23 |
| 7,608,076 B2* | 10/2009 | Ezzedine | 606/81 |
| 7,666,205 B2* | 2/2010 | Weikel et al. | 606/192 |
| 2002/0040245 A1* | 4/2002 | Lester et al. | 623/22.23 |
| 2003/0074077 A1* | 4/2003 | Taylor | 623/22.26 |
| 2003/0135215 A1* | 7/2003 | Leali | 606/72 |
| 2005/0149199 A1* | 7/2005 | Steinberg | 623/22.23 |
| 2007/0299455 A1* | 12/2007 | Stevens et al. | 606/105 |
| 2008/0215160 A1* | 9/2008 | Grundei et al. | 623/22.39 |
| 2008/0262626 A1* | 10/2008 | Raugel | 623/22.15 |
| 2009/0187252 A1* | 7/2009 | Howald et al. | 623/22.15 |
| 2009/0312807 A1* | 12/2009 | Boudreault et al. | 606/86 R |

* cited by examiner

METHODS, SYSTEMS, AND APPARATUS FOR IMPLANTING PROSTHETIC DEVICES INTO CARTILAGE

PRIORITY

The present application claims priority to U.S. Provisional Application No. 60/939,323 filed May 21, 2007, which is hereby incorporated by reference in its entirety.

TECHNICAL FIELD

Embodiments of the present disclosure relate generally to medical prosthetic devices, including prosthetic hip joint components, and associated methods of implantation and treatment.

BACKGROUND

The present disclosure relates to devices and methods of implanting medical prosthetic devices that replace at least some of the functionality of the natural hip joint. The natural hip joint is a ball-and-socket joint formed by the articulating interaction of the rounded head of the femur with the acetabulum of the pelvis. The articulating surfaces of both the head of the femur and the acetabulum are covered with articular cartilage. Various conditions can cause damage to the hip joint resulting in debilitating pain, arthritis, and/or limited mobility. In some instances, hip arthroplasty has been used to treat such conditions. Hip arthroplasty typically requires the removal of a substantial portion of bone from both the natural acetabulum and the femur to accommodate insertion of the artificial acetabular cup and the artificial femoral head. Removal of the bone can make the procedure painful, invasive, and irreversible. Accordingly, in some instances the prosthetic devices of the present disclosure are configured to be surgically implanted into a hip joint to replace at least some of the functionality of the natural hip joint, including the acetabulum, without the need to remove or damage any bone of the hip joint. Similarly, the devices and methods of the present disclosure facilitate insertion of prosthetic devices into the hip joint, in particular the acetabulum, without removing bone from the natural acetabulum.

Although existing methods and devices associated with prosthetic hip joint components have been adequate in some respects, they have not been satisfactory in all respects. The methods and devices of the present disclosure overcome one or more of the shortcomings of the existing devices and methods.

SUMMARY

In one embodiment, a method of implanting a prosthetic device into a hip joint without removing or damaging any bone of the acetabulum is disclosed.

In some instances, the prosthetic device is an implantable artificial acetabular socket made of a pliable structural material validated for medical devices used in vivo and having mechanical properties characterized by a non-linear stress-strain relationship defined by a polynomial mathematical curve having more than two coefficients, such as the Mooney Rivlin coefficients. In some instances, the material has strength and/or elasticity substantially similar to human cartilage. In some instances, the material is a polyurethane based material, which may be polycarbonate polyurethane in some embodiments, and may be a Bionate Polyurethane in some embodiments. The material of the prosthetic device and the natural articular cartilage layer operate together to dissipate bone stress and strain associated with the hip joint during the life of the device to help preserve and/or regenerate bone strength.

In another embodiment, a method of implanting a prosthetic acetabular cup into a patient is disclosed. The method comprises gaining access to an acetabulum of the patient, where the acetabulum includes an inner portion formed of bone and an outer portion formed of articular cartilage. The method also comprises creating a recess within the articular cartilage of the outer portion of the acetabulum without removing any portion of bone from the inner portion of the acetabulum. The recess is shaped to mate with a snap-fit structure of the prosthetic acetabular cup. Finally, the method comprises securely engaging the prosthetic acetabular cup with the acetabulum by snap-fitting the snap-fit structure of the prosthetic acetabular cup with the recess in the articular cartilage of the outer portion of the acetabulum. In some instances, the recess is an annular recess. In some instances, the annular recess has a depth between about 0.5 mm and about 2.0 mm. In some instances, an anchoring portion of a tool is engaged with the articular cartilage and a cutting portion of the tool is rotated about a longitudinal axis of the tool relative to the anchoring portion to form the annular recess in the articular cartilage. In some instances, securely engaging the prosthetic acetabular cup to the acetabulum comprises creating a liquid adhesion bond between the prosthetic acetabular cup and the articular cartilage of the outer portion of the acetabulum. In that regard, an outer surface of the prosthetic acetabular cup is wetted in some instances.

The specific form or geometry of the engaging surfaces of the prosthetic acetabular cup and the articular cartilage varies. For example, in some instances, the engaging surface of the prosthetic acetabular cup includes a plurality of continuous circumferential protrusions spaced about the engaging surface, and the articular cartilage is prepared with a corresponding plurality of continuous circumferential recesses for receiving the protrusions of the prosthetic acetabular cup. In another instance, the engaging surface of the prosthetic acetabular cup includes a plurality of discrete protrusions that together generally define one or more circumferential protrusion. The articular cartilage may similarly be prepared with discrete recesses for receiving the discrete protrusions of the prosthetic acetabular cup. In other instances, the articular cartilage is prepared with a continuous circumferential recess for receiving the discrete protrusions of the acetabular cup. In some embodiments, the prosthetic device includes one or more circumferential recesses—either continuous or discrete—and the articular cartilage is prepared to include a corresponding number of circumferential protrusions—either continuous or discrete—for mating the with the recesses of the prosthetic device.

Generally, the engaging surface of the prosthetic acetabular cup may include any combination of projections and/or recesses of various number, shape, size, arrangement, orientation, and/or other characteristics for engaging the prepared articular cartilage of the acetabulum. In that regard, the articular cartilage may similarly be prepared to include any combination of projections and/or recesses of various number, shape, size, arrangement, orientation, and/or other characteristics for engaging the projections/recesses of the prosthetic acetabular cup. In some instances, the articular cartilage is prepared (e.g., reamed, cut, excised, machined, etc.) at least partially hand tools for use by a surgeon. In some instances, the articular cartilage is prepared at least partially by computerized tools.

In some embodiments, the prosthetic acetabular cup includes a substantially smooth and continuous engaging surface. In such instances, the engaging surface of the prosthetic acetabular cup deforms in both a flexible phenomenon and a "creep" phenomenon, such that at least an outer portion of the device adapts to a new form matching the form of the host cartilage. In some instances, the articular cartilage is prepared with projections and/or recesses, such that after implantation the engaging surface of the prosthetic acetabular cup adapts to the projections and/or recesses of the articular cartilage to secure the prosthetic acetabular cup within the hip joint. In some instances, at least the engaging surface of the prosthetic acetabular cup deforms to securely engage the projections and/or recesses of the articular cartilage without changing the geometry of an articulating region of the prosthetic acetabular cup. In some instances, deformation of the prosthetic acetabular cup occurs immediately upon implantation of the device. In some instances, the engaging surface of the prosthetic acetabular cup flexibly deforms to substantially match the protrusions and/or recesses of the articular cartilage upon implantation (e.g., minutes, hours, or days) and the inner portions of the device adjacent the engaging surface adjust to the modified shape over an extended period of time (e.g., weeks or months).

In another embodiment, a method of implanting a pliable structural material prosthetic acetabulum into a hip joint of a patient is disclosed. The method comprises gaining access to a natural acetabulum of the patient, where the natural acetabulum includes a first outer portion formed of articular cartilage for articulating engagement with a femoral head of the patient and a second inner portion formed of bone adjacent the first outer portion. The method also comprises removing a portion of the articular cartilage of the first outer portion without damaging any bone of the second inner portion to create at least one recess within the articular cartilage. The at least one recess is sized and shaped to mate with at least one snap-fit structure of the prosthetic acetabulum. The method also comprises engaging the prosthetic acetabulum with the first outer portion of the acetabulum such that an outer engagement surface of the prosthetic acetabulum engages the first outer portion of the acetabulum via a liquid adhesion bond and the at least one snap-fit structure of the prosthetic acetabulum engages the at least one recess in the articular cartilage. Engagement of the at least one snap-fit structure of the prosthetic acetabulum prevents unwanted rotation of the prosthetic acetabulum relative to the first outer portion of the natural acetabulum. The liquid adhesion bond between the prosthetic acetabulum and the first outer portion prevents unwanted separation of the prosthetic acetabulum from the first outer portion. In some instances, between about 0.5 mm and about 2.0 mm of articular cartilage depth is removed. In some instances, the method further comprises wetting at least the outer engagement surface of the prosthetic acetabulum prior to engaging the prosthetic acetabulum with the first outer portion of the natural acetabulum. In some instances, the prosthetic acetabulum is saturated with the liquid.

In another embodiment, a method of implanting a flexible prosthetic acetabular cup into a patient is disclosed. The method comprises gaining access to the acetabulum of the patient, where the acetabulum comprising an inner portion formed of bone and an outer portion formed of articular cartilage. The method also includes determining whether the articular cartilage of the outer portion is suitable for receiving the flexible prosthetic acetabular cup. In some instances, the patient's hip joint is imaged to determine a thickness of the articular cartilage. In some instances, the thickness of the cartilage must be at least 2 mm for the articular cartilage to be considered suitable for receiving the flexible prosthetic acetabular cup. The method further comprises engaging an anchoring portion of a tool with the articular cartilage and rotating a cutting portion of the tool about a longitudinal axis of the tool relative to the anchoring portion to form a recess in the articular cartilage without removing any portion of the bone from the inner portion of the acetabulum. The recess is shaped to mate with a snap-fit structure of the flexible prosthetic acetabular cup and has a depth between about 0.5 mm and about 2.0 mm. Finally, the method comprises securing the flexible prosthetic acetabular cup to the articular cartilage. In some instances, securing the flexible prosthetic acetabular cup to the articular cartilage includes snap-fitting the snap-fit structure of the flexible prosthetic acetabular cup into the recess in the articular cartilage of the outer portion of the acetabulum.

BRIEF DESCRIPTION OF DRAWINGS

Other features and advantages of the present disclosure will become apparent in the following detailed description of embodiments of the disclosure with reference to the accompanying of drawings, of which.

DETAILED DESCRIPTION

Figure 1:
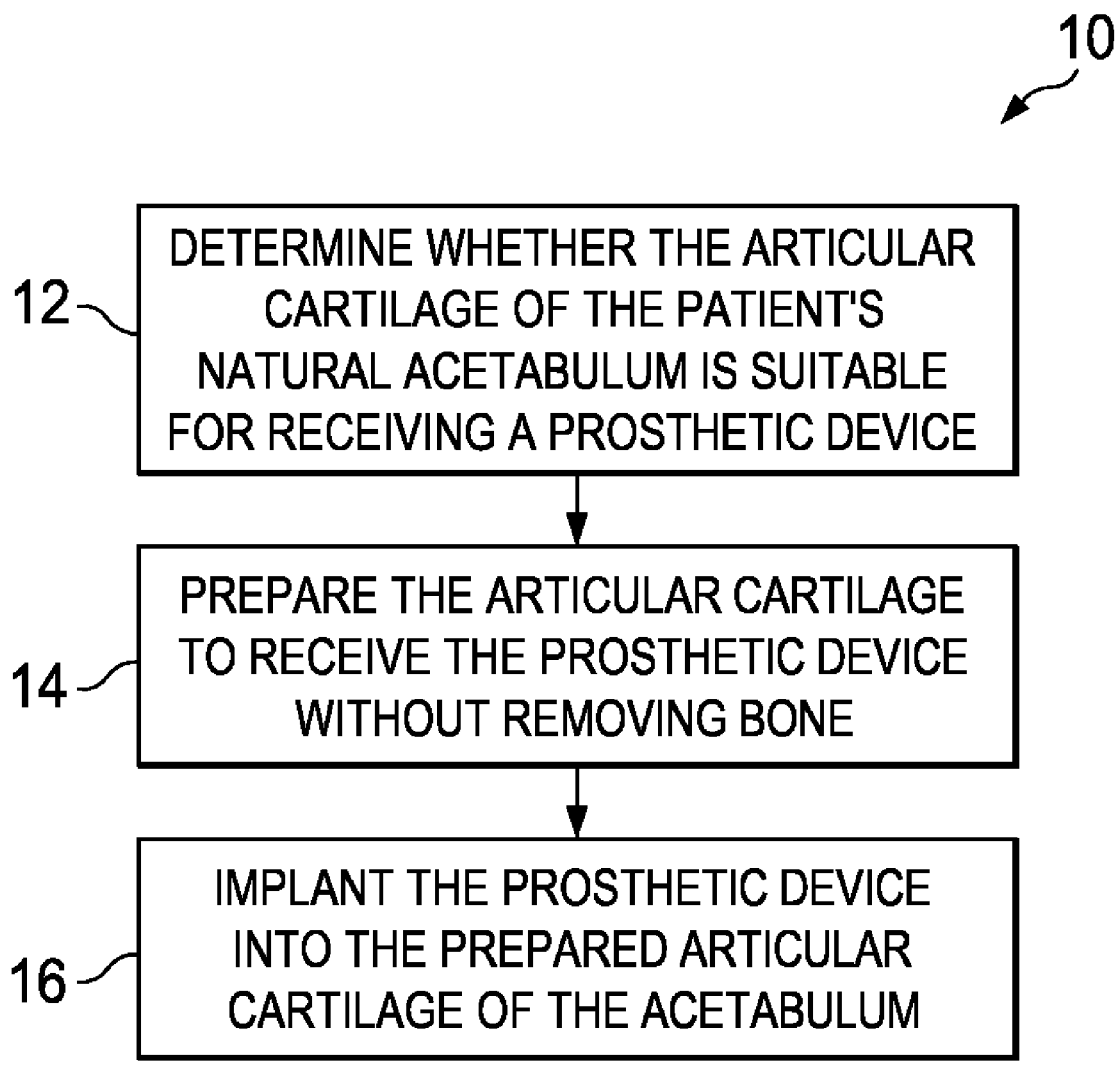
FIG. 1 is a flowchart representative of a method according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Referring now to FIG. 1 shown therein is a flowchart representative of a method 10 according to one embodiment of the present disclosure. In that regard, the method 10 begins at step 12 with the determination of whether the articular cartilage of a patient's natural acetabulum is suitable for receiving a prosthetic device in accordance with the present disclosure. In that regard, the thickness and/or health of the articular cartilage may be considered in determining whether the articular cartilage is suitable for receiving a prosthetic device. In some instances, characteristics of the articular cartilage are determined pre-operatively using medical imaging. For example, in some instances MRI renderings of the patient's hip joint are utilized to determine the thickness and/or condition of the articular cartilage of the acetabulum. In other instances, other medical imaging techniques are utilized. In some instances, the thickness and/or condition of the articular cartilage is assessed using the methods and systems similar to those disclosed in U.S. Pat. No. 7,184,814 titled "ASSESSING THE CONDITION OF A JOINT AND ASSESSING CARTILAGE LOSS," which is hereby incorporated by reference in its entirety. Further, in some embodiments the thickness and/or condition of the articular cartilage is confirmed during the surgical procedure itself to ensure that the articular cartilage is suitable for receiving the prosthetic device. In some instances, no pre-operative imaging of the articular cartilage is undertaken and the articular cartilage is evaluated only during the surgery.

In some instances, the thickness and/or condition of the articular cartilage is utilized to determine which of a library of prosthetic devices is capable or desirable for use with a specific patient. For example, in one specific example a first preferred prosthetic device requires a healthy articular cartilage thickness of at least 2.5 mm while a second preferred prosthetic device requires a healthy articular cartilage thickness of at least 1.5 mm. Accordingly, in some instances the thickness and health of the articular cartilage will dictate which of the first and second prosthetic devices is best suited for implantation into the patient's acetabulum. Generally, a patient must have healthy articular cartilage with a thickness of at least 1.0 mm to be considered suitable for receiving a prosthetic device without causing damage to the underlying bone in accordance with the present disclosure. In some instances, a patient must have healthy articular cartilage with a thickness of at least 2.0 mm to be considered suitable for receiving a prosthetic device without causing damage to the underlying bone in accordance with the present disclosure.

In some embodiments of the present disclosure, the prosthetic acetabular components include one or more projections extending from and outer engagement surface, where the maximum height of the projections from the engagement surface can be considered the projection height. In such embodiments, the articular cartilage can be evaluated to determine whether the cartilage has a thickness greater than or equal to the projection height. If the articular cartilage has a thickness greater than or equal to the projection height, then the articular cartilage is suitable for receiving the prosthetic device. However, if the articular cartilage has a thickness less than the projection height such that a bony portion of the acetabulum must be removed in order for the acetabulum to securely receive the prosthetic acetabular cup, then the articular cartilage is not considered suitable for receiving that prosthetic device. In such instances, the articular cartilage may be suitable for receiving a prosthetic device with projections having a lower projection height. In some instances, a prosthetic device with a plurality of projections having a lower projection height is utilized. In some instances, a surgeon may decide to remove at least a minimal amount or volume of bone in addition to the articular cartilage. Accordingly, in such instances at least a portion of the projections of the prosthetic device may engage a portion of the bone while the substantial majority of the outer surface of the prosthetic device engages the articular cartilage of the patient. In some instances, the projections of the device are particularly suited for engaging bone while the outer surface is engaged only with the articular cartilage.

It is recognized that a patient's articular cartilage does not always have a uniform thickness across the acetabulum due to uneven wear, degradation, or otherwise. Accordingly, in some instances specific portions of the articular cartilage are evaluated. For example, in some instances the prosthetic device includes one or more engagement structures (e.g., projections and/or recesses) for engaging one or more prepared portions in the articular cartilage (e.g., recesses and/or projections). Accordingly, the portions of the articular cartilage positioned where the one or more prepared portions are to be formed are evaluated. Based on the characteristics of the articular cartilage where the prepared portions are to be formed, a determination of whether the articular cartilage is suitable for a particular prosthetic device can be made. Since different prosthetic devices will have different engagement structures and/or different engagement structure layouts, the overall characteristics of the articular cartilage are utilized to identify the prosthetic devices most suitable for use with the patient's articular cartilage. In some instances, a mapping or 3-D rendering of the articular cartilage is created. The mapping or 3-D rendering is subsequently used to model or simulate the interaction of one or more prosthetic devices with articular cartilage. Similarly, the mapping or 3-D rendering is utilized in some instances to evaluate various techniques or approaches to preparing the articular cartilage to receive a prosthetic device. In that regard, in some instances a desirable preparation technique or approach is identify through the simulation or modeling and is subsequently executed via a computer-guided and/or computer-aided surgical technique corresponding to the desired preparation. In other instances, the desired preparation as identified by the simulation is performed by a surgeon without computer-guided assistance.

Referring again to FIG. 1, the method 10 continues at step 14 with preparation of the articular cartilage of the natural acetabulum to receive the prosthetic device. In accordance with the present disclosure, none of the bone of the natural acetabulum is removed or damaged in preparing the acetabulum to receive the prosthetic device. In this manner, the methods of the present disclosure help to preserve as much of the natural bone structure of the patient's natural acetabulum as possible. Accordingly, in some instances preparation of the hip joint comprises preparing a portion of the articular cartilage of the patient without damaging the underlying bony portion of the acetabulum. In some instances, one or more recesses are created in the articular cartilage. In that regard, each of the recesses may be sized and shaped to engage a corresponding structural element of the prosthetic device that is to be inserted into the hip joint. In some instances the prosthetic device is similar to one or more of the prosthetic devices described in U.S. patent application Ser. No. 10/289,126 titled "ONE PIECE SNAP FIT ACETABULAR CUP," U.S. patent application Ser. No. 10/497,897 titled "CUSHION BEARING IMPLANTS FOR LOAD BEARING APPLICATIONS," U.S. patent application Ser. No. 10/515,486 titled "IMPLANTS," U.S. patent application Ser. No. 11/688,153 titled "CERAMIC-ON-CERAMIC PROSTHETIC DEVICE COUPLED TO A FLEXIBLE BONE INTERFACE," or PCT Application No. PCT/IL2006/000343 titled "IMPLANT DEVICES" (published as WO 2006/097932), each incorporated by reference in its entirety. Similarly, in some instances one or more projections are created in the articular cartilage, each of the projections sized and shaped to engage a corresponding structural element of the prosthetic device.

In some embodiments the articular cartilage is prepared to receive a snap-fit structure of the prosthetic device that is utilized to assist in securing the device within hip joint without penetrating bone. In that regard, the articular cartilage may be reamed, machined, cut, excised, compressed, and/or otherwise modified to include one or more recesses of various shapes and sizes to mate with corresponding snap-fit structure of a prosthetic device. Generally, the number, size, and shape of the recesses is dictated by the prosthetic device to be implanted. In some instances, one or more surgical tools are utilized to create the one or more recesses in the articular cartilage. In some instances, the tools are similar to those described in U.S. patent application Ser. No. 10/497,897 titled "CUSHION BEARING IMPLANTS FOR LOAD BEARING APPLICATIONS," U.S. patent application Ser. No. 11/688,153 titled "CERAMIC-ON-CERAMIC PROSTHETIC DEVICE COUPLED TO A FLEXIBLE BONE INTERFACE," or PCT Application No. PCT/IL2006/000343 titled "IMPLANT DEVICES" (published as WO 2006/097932), each incorporated by reference in its entirety. In that regard, the tools described in those applications may be specifically modified for preparation of articular cartilage instead of bone. For example, in some instances the cutting blades or similar features are sharper than those utilized for bone removal in order to increase the precision of the reaming/cutting utilized to create the recess. Also, the anchoring features of the tools utilized to the hold the tool in place relative to the acetabulum during the preparation may be dulled or otherwise modified to prevent unwanted damage to the articular cartilage or surrounding hip joint anatomy. In some instances, the tools as described in those applications are utilized without modification to prepare the articular cartilage.

Figure 2:
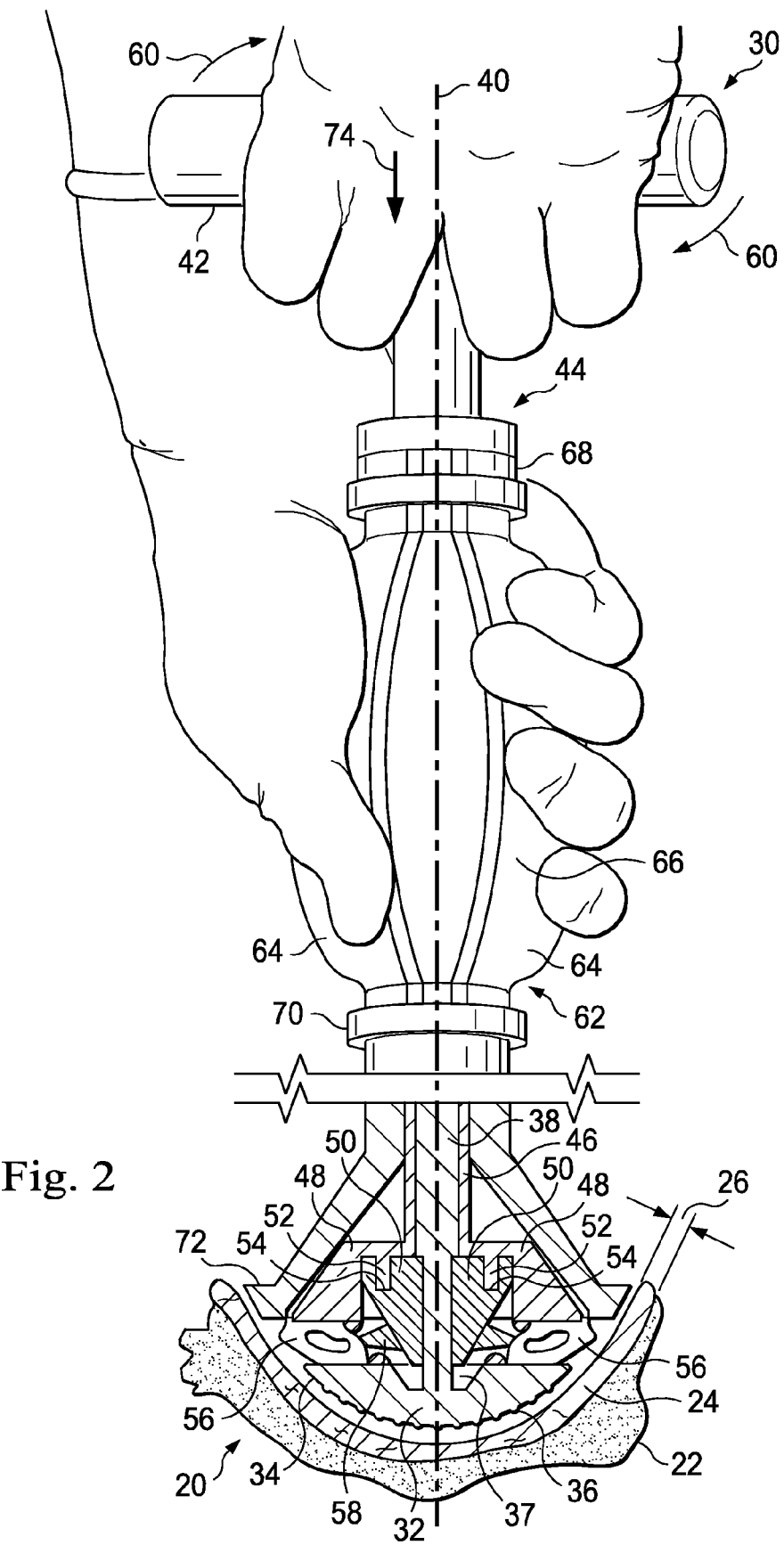
FIG. 2 is a diagrammatic, partial cross-sectional side view of a tool preparing the articular cartilage of a natural acetabulum according to one embodiment of the present disclosure.
Figure 3:
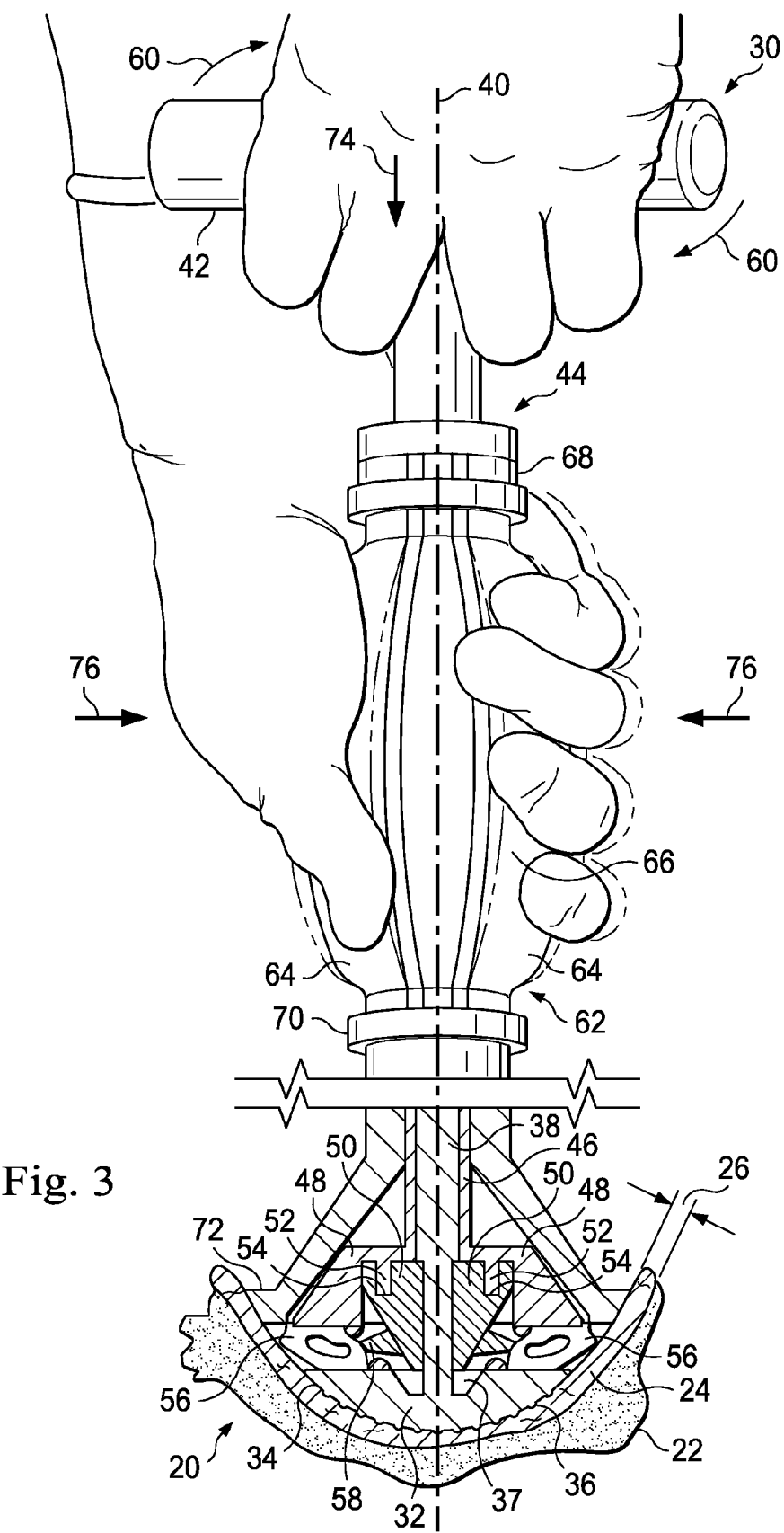
FIG. 3 is a diagrammatic, partial cross-sectional side view of a subsequent stage of the tool of FIG. 2 preparing the articular cartilage of the natural acetabulum.
Figure 4:
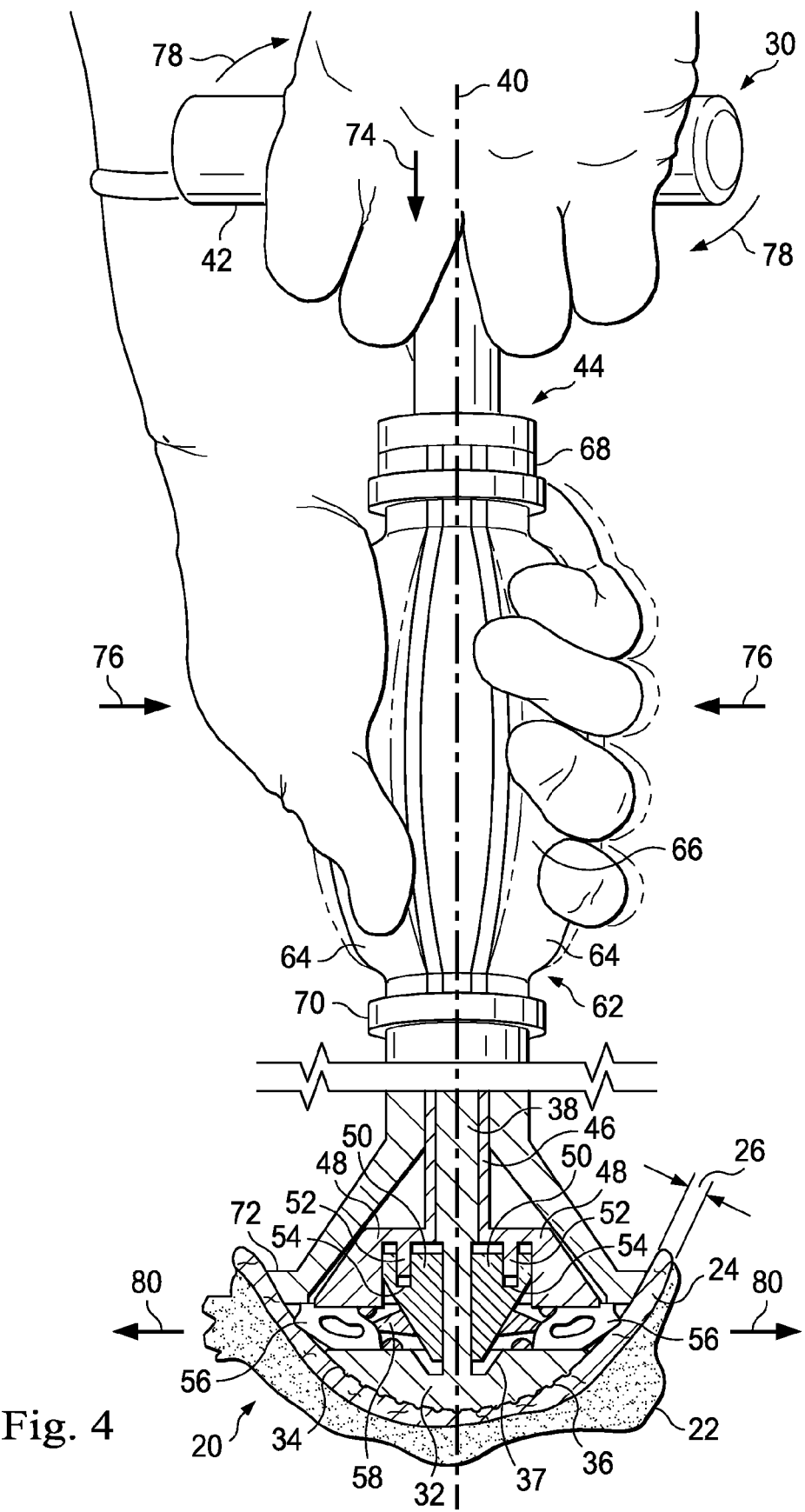
FIG. 4 is a diagrammatic, partial cross-sectional side view of a subsequent stage of the tool of FIGS. 2 and 3 preparing the articular cartilage of the natural acetabulum.
Figure 5:
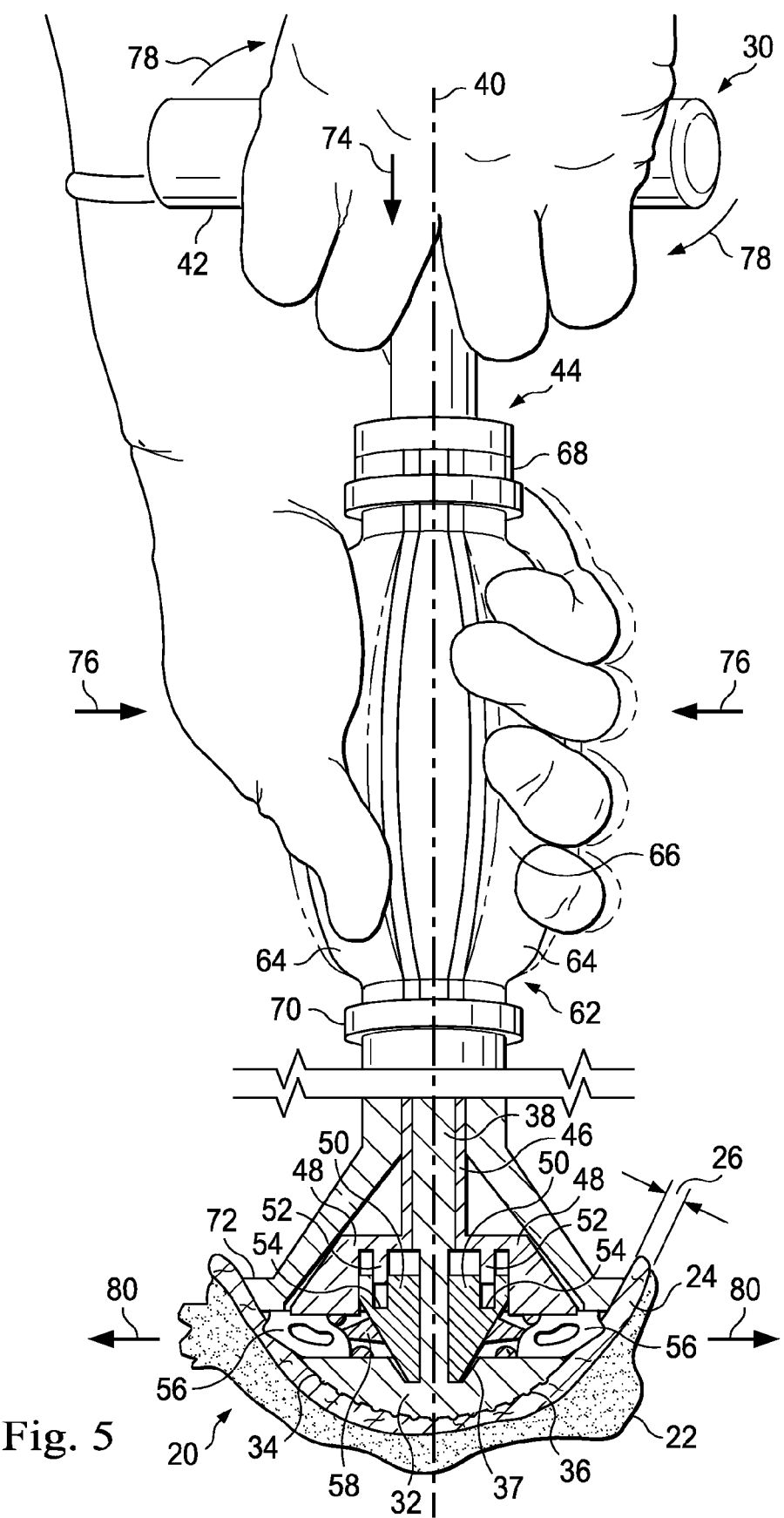
FIG. 5 is a diagrammatic, partial cross-sectional side view of a subsequent stage of the tool of FIGS. 2, 3, and 4 preparing the articular cartilage of the natural acetabulum.

Referring now to FIGS. 2-5, shown therein are various partial cross-sectional side views of a natural acetabulum 20—comprised of an inner portion 22 formed of bone and an outer portion 24 formed of articular cartilage and generally having a thickness 26—being prepared by a tool 30 according to one embodiment of the present disclosure. Specifically, FIG. 2 is a diagrammatic, partial cross-sectional side view of the tool 30 preparing the articular cartilage 24 of the natural acetabulum 20; FIG. 3 is a diagrammatic, partial cross-sectional side view of a stage subsequent to that of FIG. 2 of the tool 30 preparing the articular cartilage 24 of the natural acetabulum 20; FIG. 4 is a diagrammatic, partial cross-sectional side view of a stage subsequent to that of FIG. 3 of the tool 30 preparing the articular cartilage 24 of the natural acetabulum 20; and FIG. 5 is a diagrammatic, partial cross-sectional side view of a stage subsequent to that of FIG. 4 of the tool 30 preparing the articular cartilage 24 of the natural acetabulum 20.

Referring more specifically to FIG. 2, the articular cartilage 24 is shown as having a substantially uniform thickness 26. Generally, the thickness 26 of the articular cartilage 24 of a healthy acetabulum is approximately 4 mm or less. While the articular cartilage 24 is shown as having a substantially uniform thickness 26 it is recognized that the thickness of the articular cartilage will have slight to substantial variations across the acetabulum 20. Accordingly, while the articular cartilage 24 is shown and at times discussed as having a substantially uniform thickness 26 it is understood that the present disclosure is equally applicable to articular cartilage 24 with a non-uniform thickness.

In some instances, preparation of the articular cartilage 24 at step 14 includes removing portions of the articular cartilage to define a substantially uniform surface prior to additional preparation of the articulating cartilage. In some instances, the uniform surface is partially spherical. That is, the uniform surface is defined as a portion of an outer surface of a sphere. In some particular embodiments, the uniform surface is substantially semi-spherical. In that regard, the articular cartilage is reamed to create the uniform surface in some embodiments. In such instances the amount of cartilage removed is limited to that necessary to create the uniform surface. It is generally desirable to remove as little healthy articular cartilage as possible. However, in some instances it is desirable to remove damaged and/or unhealthy articular cartilage, which may require removal of some healthy cartilage as well to create the uniform surface. In other instances, the natural surface of the articular cartilage is utilized such that the surface is not necessarily uniform.

As shown in FIG. 2, the tool 30 includes an anchoring element 32 having an outer surface 34 with a plurality of cartilage-engaging protrusions 36 extending therefrom. Each of the protrusions 36 includes a rounded tip such that the protrusions can engage the articular cartilage 24 sufficiently to prevent unwanted movement of the tool 30 without causing damage to the articular cartilage surface. In that regard, in some instances the protrusions 36 are sized and shaped to temporarily deform the cartilage without penetrating or otherwise permanently altering the cartilage. Opposite the outer engagement surface 34, the anchoring element 32 includes a recessed portion 37. The tool 30 also includes a central shaft 38 extending proximally along an axis 40 away from the anchoring element 32 towards a handle 42. Mounted for rotation about central shaft 38 is a rotational driving assembly 44 including the handle 42 and an elongate hollow shaft 46 that is sized to rotationally accommodate central shaft 38. The hollow shaft 46 terminates in rotational driving plate 48. Coupled to rotational driving plate 48 is a conical rotational and axial driving element 50. In some instances the driving element 50 threadingly engages the central shaft 38. In some instances, the rotational driving plate 48 is formed with one or more pins 52 that extend into corresponding sockets 54 formed in driving element 50 that maintain the rotational driving plate 48 and the driving element 50 in axial alignment along the longitudinal axis 40. A plurality of cutting elements 56 are each slidably received within a pair of channels defined by the driving plate 48 and the driving element 50. The cutting elements are mounted on a resilient support ring 58 which permits simultaneous radially outward and rotational displacement of the cutting elements 56 in response to simultaneous axial and rotational movement of driving element 50 in threaded engagement with central shaft 38 in response to rotation of the handle 42 in a direction indicated by an arrow 60.

The tool 30 also includes a radially displaceable cartilage engagement assembly 62, typically comprises a plurality of integrally formed flexible engagement elements 64, each comprising a hand engageable portion 66 lying between an proximal retaining portion 68 and a distal retaining portion 70. The assembly 62 also includes a radially expandable cartilage engaging portions 72. In some instances, the assembly 62 includes six integrally formed flexible engagement elements 64 that are held together about hollow shaft 46 at the retaining portions 68 and 70. As will be described herein below in greater detail, an operator, such as a surgeon, grasping second handle hand engageable portion 66 with one hand causes inward bending of flexible engagement elements 64, which causes cartilage engaging portions 72 to be displaced radially outwardly into retaining engagement with the walls of the articular cartilage being prepared. In this manner the assembly 62 may be used in addition to or in lieu of the anchoring element 32 to prevent unwanted movement of the tool 30 during preparation of the articular cartilage. In one specific example, the anchoring element 32 does not include projections 36 such that anchoring element alone may be insufficient to prevent unwanted movement of the tool 30. In such an embodiment, the assembly 62 is utilized to stabilize the tool 30 during preparation of the articular cartilage.

As shown in FIG. 2, a surgeon or other medical professional initially places the tool 30 and anchoring element 32 into engagement with the articular cartilage 24 of the acetabulum 20 and urges the handle 42 towards the articular cartilage as indicated by an arrow 74, causing the protrusions 36 on engagement surface 34 to engage the articular cartilage without causing damage to the articular cartilage. This engages the anchoring element 32 to the articular cartilage, thereby resisting unwanted movement of the tool 30 with respect to articular cartilage 24.

Referring now to FIG. 3, the cartilage engaging portions 72 of the assembly 62 have been extended radially to engage side surfaces of the articular cartilage 24. This engagement is produced by the surgeon or other medical professional squeezing the hand engageable portion 66 inward as indicated by arrows 76, producing corresponding radially outward displacement of cartilage engaging portions 72 into retaining engagement with the side surfaces of the articular cartilage 24. This further stabilizes the tool 30 and resists unwanted movement with respect to the acetabulum 20.

Referring now to FIG. 4, shown therein is the beginning of a reaming operation for creating an annular recess in the articular cartilage 24. Rotation of the handle 42 about axis 40 such as in a direction indicated by arrows 78 causes a similar rotation of driving element 50 about axis 40, which results in axial displacement distally of driving element 50 due to its threaded engagement with central shaft 38. This distal displacement of driving element 50 urges the cutting elements 56, which are slidably seated in the channels of the driving element 50 and the driving plate 48, in a radially outward direction, as indicated by arrows 80, into cutting engagement with the articular cartilage 24. The cutting elements 56 also rotate around the axis 74 with the since the cutting elements are received within the channels of the driving plate 48. Accordingly, as the handle is rotated the cutting elements 56 rotate about the axis 74 and extend radially outward into the articular cartilage 24. Upon contacting the articular cartilage 24 the cutting elements will continue to cut or remove articular cartilage as the handle 42 and, in turn, the cutting elements 56 are further rotated about the axis 40. In this manner, the amount of articular cartilage 24 removed gradually increases as the cutting elements are radially displaced outwardly and the handle 42 is further rotated about the axis 40. In this manner the cutting elements 56 are utilized to ream the annular recess into the articular cartilage 24 of the acetabulum without penetrating the bone 22.

Referring now to FIG. 5, shown therein is a substantially completed reaming operation produced by rotation of the handle 42 about axis 40. Continued rotation of the handle 42 causes rotation of the driving element 50 about axis 40 and corresponding distal axial displacement of the driving element 50 due to the threaded engagement with the central shaft 38 as discussed above. As the driving element is urged further distally, the cutting elements 56 are urged further radially outward. The axial displacement of the driving element 50 typically stops when the driving element 50 engages the bottom of the recessed portion 37 formed in the anchoring element 32 opposite the engagement surface 34. At this point the cutting elements 56 are at a maximum radial displacement. In some embodiments, the maximum radial displacement of the cutting elements 56 corresponds with a desired depth of the annular recess being formed in the articular cartilage 24. For example, in some instances the cutting elements 56 are configured to be displaced radially such that a recess having a depth between about 0.5 mm and about 2.0 mm is created in the articular cartilage. In other instances, the cutting elements 56 are displaced to a lesser or greater extent. In that regard, the depth of the recessed portion 37 of the anchoring element 32, the angle of the conical aspect of the driving element 50, and/or other aspects of the tool are sized to create a desired maximum outward radial displacement of the cutting elements 56.

In some instances, the maximum outward radial displacement of the cutting elements 56 is adjustable such that a surgeon can select the maximum displacement corresponding to a prosthetic device that is to be implanted. In that regard, in some instances the maximum outward radial displacement of the cutting elements is set such that the radius of the cutting elements as measured from axis 40 is less than the spherical radius of the boundary between the bone and the articular cartilage, such that even at maximum displacement the cutting elements will not reach the bone. In this manner, accidental or unintended removal of bone is limited. In some instances, one or more sizing cups are utilized to set the maximum displacement of the cutting elements 56. The sizing cups are generally made of material sufficiently hard to prevent penetration by the cutting elements. In some instances, cutting elements are extended outwardly until they contact the sizing cup at which point the maximum displacement of the cutting elements is set. The particular sizing cup chosen is based on the patient's anatomy as determined using imaging techniques or otherwise. In other instances, a plurality of tools 30 having different maximum radial displacements are provided. In some instances, the tools 30 have a radial displacement of the cutting elements that is associated with a particular prosthetic device, such that a particular tool is to be used with a particular device. Further, it is appreciated that the extension and retraction of cutting elements 56 may be monitored by a gauging apparatus that is viewable by the operator of the tool 30. The gauging apparatus may be mechanical or electronic.

Though not explicitly shown, disengagement and removal of the tool 30 may readily be accomplished by reversing the steps described above for preparing the articular cartilage. For example, rotating the first handle in an opposite direction such that the cutting elements 56 are retracted. The resiliency of ring 58 is operative to radially retract the cutting portions 56 upon the proximal axial displacement of the driving element 50. Further, releasing the hand engageable portion 66 causes the cartilage engaging portions 72 to disengage the articular cartilage. Subsequently, the tool 30 can simply be lifted such that the anchoring element 32 disengages the articular cartilage 24.

As discussed above, it is appreciated that control of the tool 30 may at least partially be computer guided or aided. Further still, rotation of elongate hollow shaft 46 and driving plate 50 may be controlled or actuated by an electronic or hydraulic system, and the operator may utilize the display of extension and retraction of the cutting elements to determine the completion of annular recess to a precise desired depth. In this manner, the electronic or hydraulic system may replace handle 42. In other instances, the preparation may be performed substantially by the tool 30 being controlled by a computer system.

Figures 6, 7:
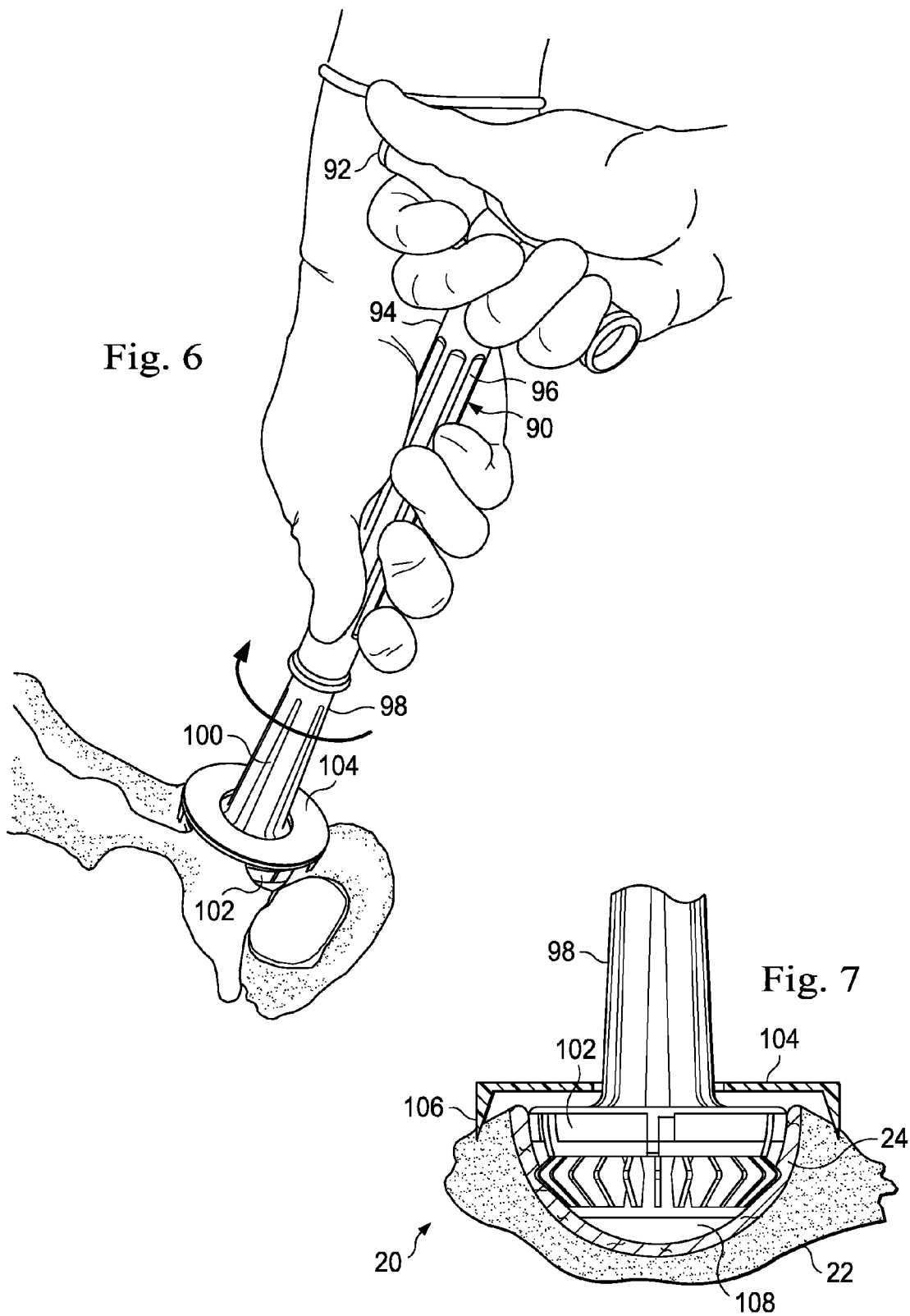
FIG. 6 is a diagrammatic perspective view of a tool preparing the articular cartilage of a natural acetabulum according to another embodiment of the present disclosure.
FIG. 7 is a diagrammatic, partial cross-sectional side view of the tool of FIG. 6 preparing the articular cartilage of the natural acetabulum.

Referring now to FIGS. 6 and 7, shown therein is the natural acetabulum 20—comprised of the inner portion 22 formed of bone and the outer portion 24 formed of articular cartilage and generally having the thickness 26—being prepared by a tool 90 according to another embodiment of the present disclosure. Specifically, FIG. 6 is a diagrammatic perspective view of the tool 90 preparing the articular cartilage 24 of the natural acetabulum 20 and FIG. 7 is a diagrammatic, partial cross-sectional side view of FIG. 6.

The tool 90 is provided with a handle 92 fixedly coupled to a shaft 94. An elongate gripping portion 96 is rotatably and slidably mounted over shaft 94 and axially engages a plurality of outwardly extendible engagement elements 98, which are also rotatably and slidably mounted with respect to shaft 94. The outwardly extendible engagement elements 98 are spaced by a plurality of axially extending slots 100. The outwardly extendible engagement elements 98 include engagement features 102 extending from distal portions of the elements 98. The engagement features 102 are for engaging the articular cartilage after outward displacement of the elements 98. In that regard, the engagement features 102 are sized and shaped to engage the articular cartilage without causing permanent damage to the articular cartilage. In some instances, the engagement features comprise a roughened surface (e.g., knurled, grit blasted, diamond patterned, or otherwise) for frictionally engaging the articular cartilage. In some instances, the outwardly extendable engagement elements 98 are displaced radially outward upon axial movement in a distal direction. In that regard, the axial movement of the engagement elements 98 is directly controlled by the position of the gripping portion 96 in some instances. In some embodiments, the gripping portion 96 and the engagement elements 98 are integrally formed.

Positioned around the outwardly extendable engagement elements 98 is an anchoring mechanism 104. The anchoring mechanism 104 is generally disc shaped and includes a plurality of engagement features 106 extending distally. In that regard, the engagement features 106 are configured to engage the bony portions of the acetabulum 20 positioned surrounding the socket defined by the articular cartilage 24. The engagement features 106 are spikes for penetrating the bone in some instances. In other embodiments, the engagement features 106 comprise other types of protrusions for engaging the bone. The anchoring mechanism 104 is moveable axially and rotationally relative to the shaft 94. In some embodiments, the anchoring mechanism 104 is connected or integral to the distal portions of engagement elements 98 such that the anchoring mechanism is axially displaced along with the engagement elements. In some such embodiments, the anchoring mechanism 104 does not extend outwardly along with engagement elements, but rather has fixed dimensions relative to the shaft 94. Using the anchoring mechanism 104, the tool 90 can be securely engaged to the acetabulum to prevent unwanted movement of the tool 90 without damaging the articular cartilage 24 that will receive the prosthetic device. In that regard, while the tool 90 is shown with engagement features 102 and a anchoring portion 108 (similar to anchoring element 32 of tool 30), in other embodiments these features are not present and the anchoring mechanism 104 is the primary anchoring or stabilizing feature of the tool 90. In that regard, the number of engagement features 106 extending from the anchoring mechanism 104 varies. In some specific embodiments, the anchoring mechanism 104 includes any where from 1 to 12 engagement features 106. In other embodiments, the anchoring mechanism 104 includes additional engagement features. With the tool 90 stabilized relative to the acetabulum to prevent unwanted movement of the tool, the articular cartilage can then be prepared in a manner similar to those described above.

Referring again to FIG. 1, the method 10 continues at step 16 with implanting the prosthetic device into the prepared articular cartilage 24 of the acetabulum. As discussed above, generally in most cases none of the bone 22 of the natural acetabulum 20 is removed or damaged in preparing the acetabulum to receive the prosthetic device. In this manner, the methods of the present disclosure help to preserve as much of the natural bone structure of the patient's natural acetabulum 20 as possible. As described above, one or more recesses may be created in the articular cartilage and, in some instances, may be sized and shaped to engage a corresponding structural element of the prosthetic device is similar to one or more of the prosthetic devices described in U.S. patent application Ser. No. 10/289,126 titled "ONE PIECE SNAP FIT ACETABULAR CUP," U.S. patent application Ser. No. 10/497,897 titled "CUSHION BEARING IMPLANTS FOR LOAD BEARING APPLICATIONS," U.S. patent application Ser. No. 10/515,486 titled "IMPLANTS," or PCT Application No. PCT/IL2006/000343 titled "IMPLANT DEVICES" (published as WO 2006/097932), each incorporated by reference in its entirety. Implantation of some exemplary prosthetic devices having a specific type of snap-fit feature will now be described. However, no limitation is intended thereby and it is understood that other prosthetic devices may be implanted in a similar manner.

In some embodiments, the prosthetic acetabular cup includes a substantially smooth and continuous engaging surface. In such instances, the articular cartilage is prepared with projections and/or recesses, such that after implantation the engaging surface of the prosthetic acetabular cup adapts to the projections and/or recesses of the articular cartilage to secure the prosthetic acetabular cup within the hip joint. In some instances, at least the engaging surface of the prosthetic acetabular cup deforms to securely engage the projections and/or recesses of the articular cartilage without changing the geometry of the inner articulating surface of the prosthetic acetabular cup. In some instances, at least the engaging surface of the prosthetic acetabular cup deforms to securely engage the projections and/or recesses of the articular cartilage without changing the geometry of the inner articulating surface or adjacent portions of the prosthetic acetabular cup. For example, in some instances, at least an area having a thickness between about 0.5 mm and about 1.0 mm adjacent the inner articulating surface is not affected by deformation of the outer portion of the device. In some instances, deformation of the prosthetic acetabular cup occurs immediately upon implantation of the device. In some instances, the engaging surface of the prosthetic acetabular cup flexibly deforms to substantially match the protrusions and/or recesses of the articular cartilage upon implantation (e.g., minutes, hours, or days) and the inner portions of the device adjacent the engaging surface adjust to the modified shape over an extended period of time (e.g., weeks or months).

Figure 8:
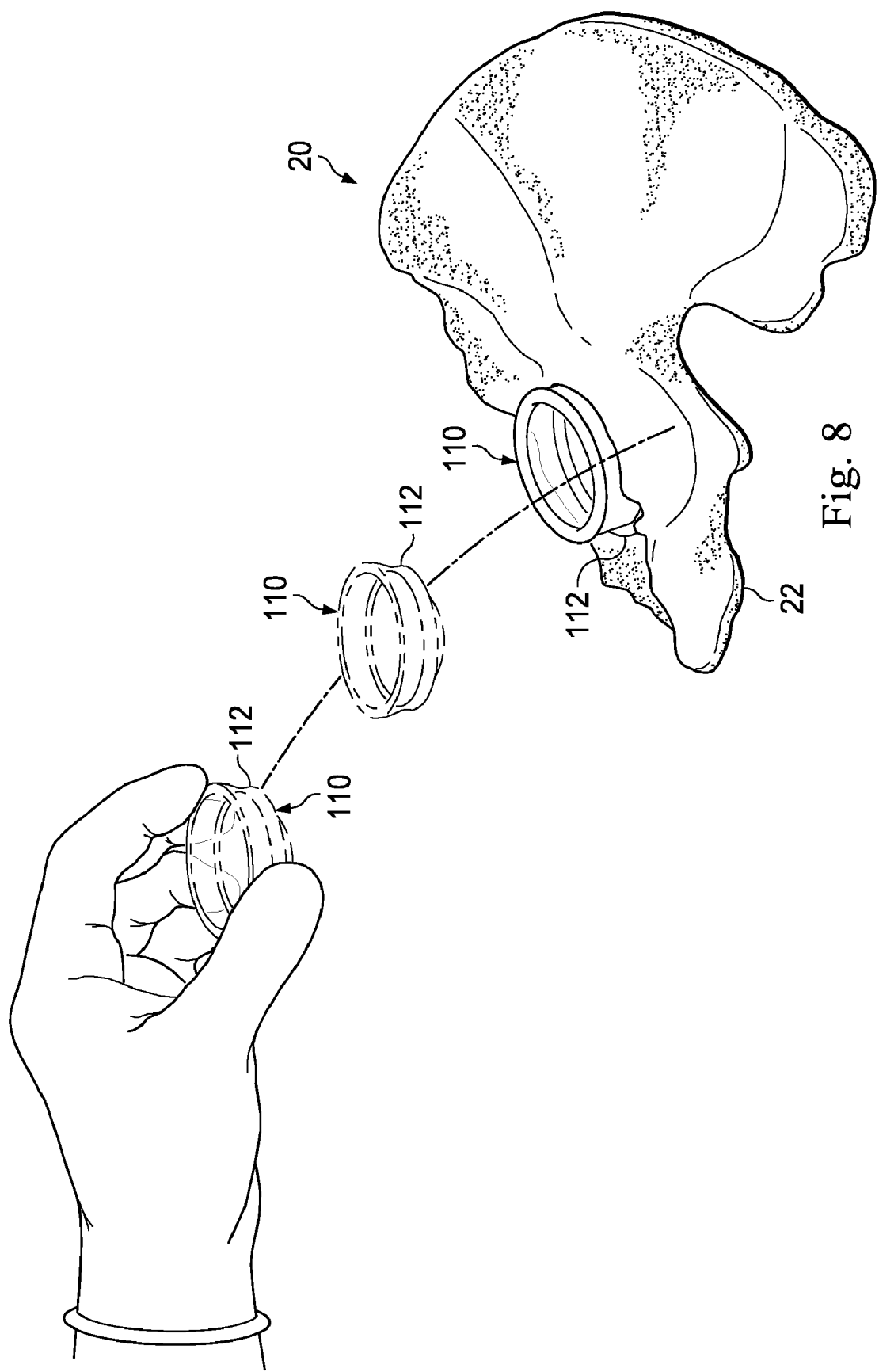
FIG. 8 is a diagrammatic perspective view of a process of implanting a prosthetic device into the prepared articular cartilage of a natural acetabulum according to one aspect of the present disclosure.
Figure 9:
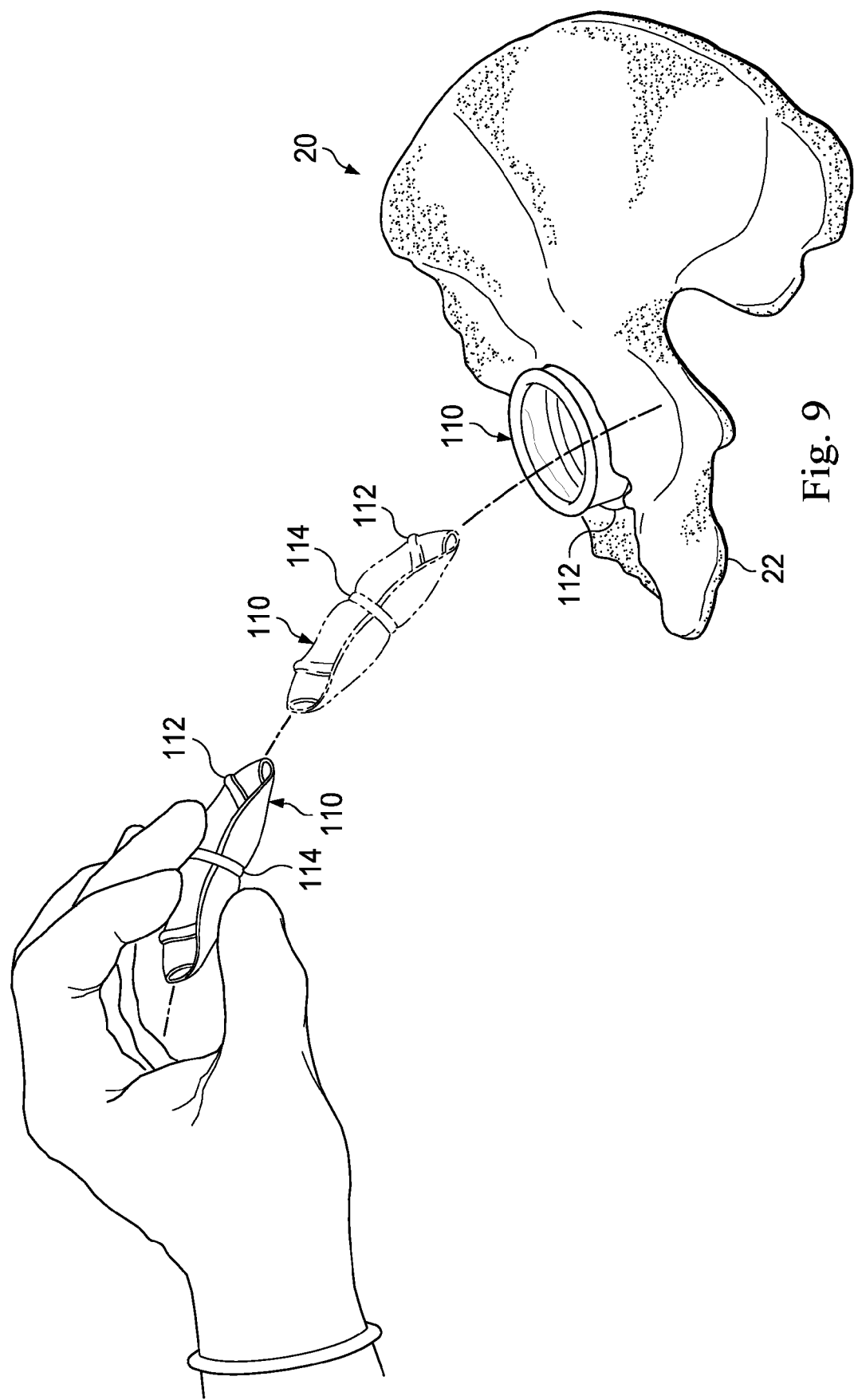
FIG. 9 is a diagrammatic perspective view of a process of implanting a prosthetic device into the prepared articular cartilage of a natural acetabulum similar to that of FIG. 8, but showing an alternative embodiment of the present disclosure.

Referring more specifically to FIG. 8, shown therein is a perspective series view of the introduction and pre-snap-fit placement of an implantable prosthetic acetabular socket 110 into the prepared acetabulum 20 according to one aspect of the present disclosure. The prosthetic acetabular socket 110 includes a snap-fit structure 112 on an outer surface. In the illustrated embodiment the snap-fit structure 112 comprises an annular protrusion extending around a perimeter of the socket 110 between the rim and the apex of the socket that is configured to snap-fit into engagement with the recess prepared in the articular cartilage 24 of the acetabulum 20. Referring more specifically to FIG. 9, shown therein is a perspective series view of the introduction and pre-snap-fit placement of the implantable prosthetic acetabular socket 110 into the prepared acetabulum 20 according to another aspect of the present disclosure. In the embodiment of FIG. 9, the acetabular socket 110 is introduced in a folded configuration. In that regard, a flexible and breakable band 114 is utilized in some instances to maintain the acetabular socket 110 in the folded configuration during insertion. Once positioned adjacent the acetabulum the band 114 is removed and the resiliency of the acetabular socket 110 causes the socket to return to its natural configuration. In other embodiments, the acetabular socket 110 is maintained in the folded configuration by the surgeon's hand, a tool, or otherwise. The resultant positioning of the socket 110 is the same in both FIGS. 8 and 9. Use of the folded configuration as shown in FIG. 9 is particularly suitable for minimally invasive surgical approaches.

Figure 10:
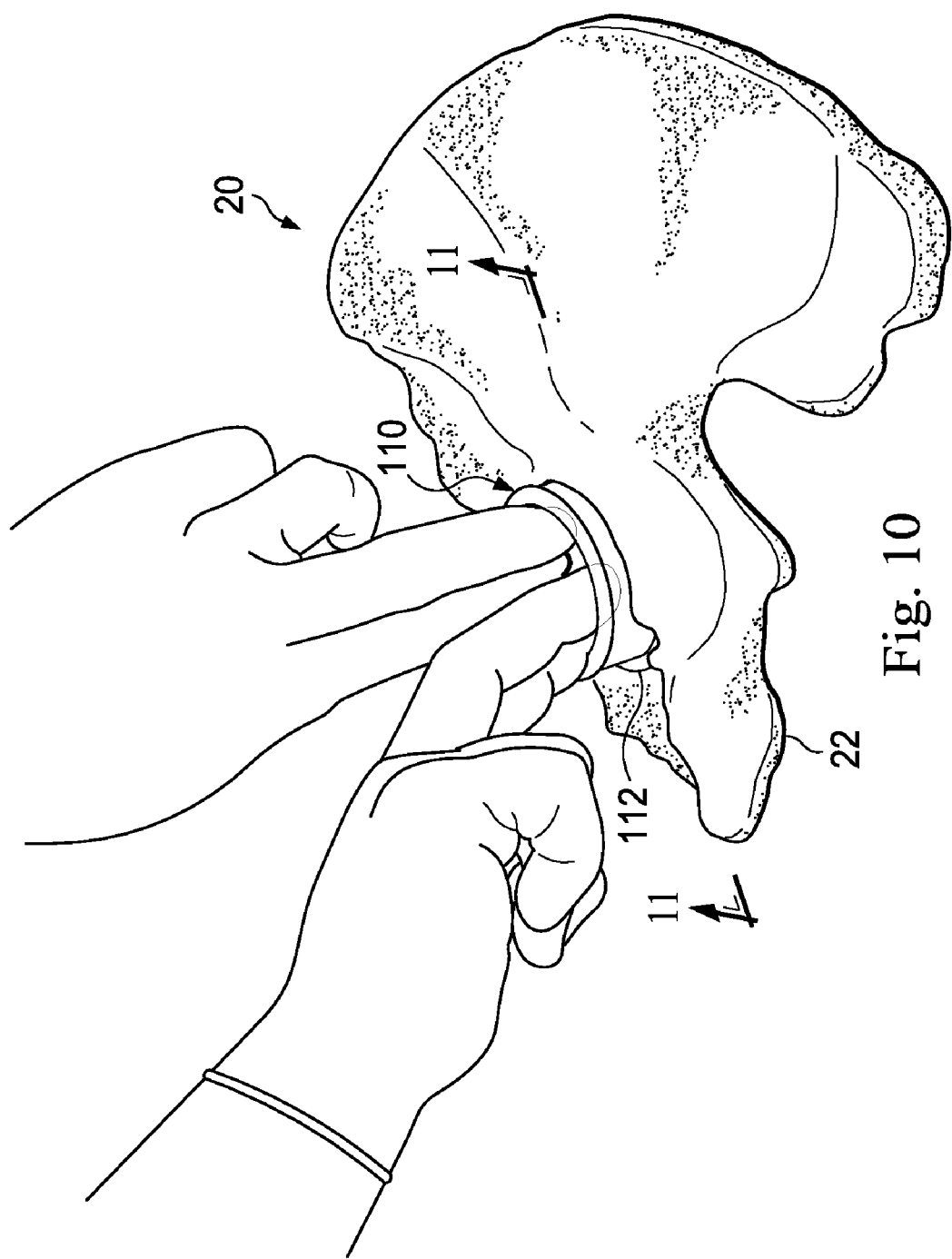
FIG. 10 is a diagrammatic perspective view of a step of securely implanting a prosthetic device into the prepared articular cartilage of a natural acetabulum according to one embodiment of the present disclosure.
Figure 11:
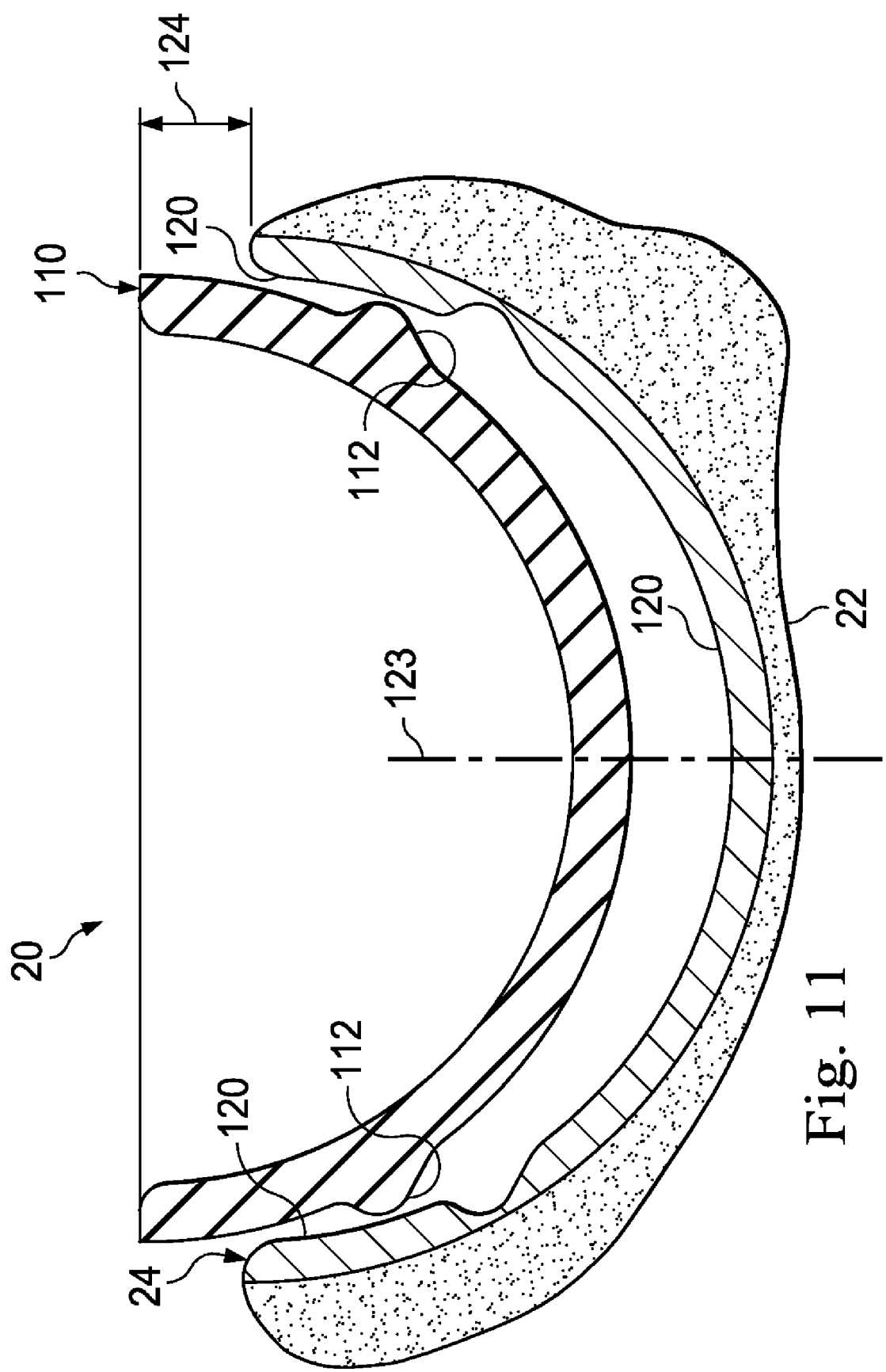
FIG. 11 is a diagrammatic cross-sectional view of a stage of the prosthetic device being implanted into the prepared articular cartilage of the natural acetabulum according to one embodiment of the present disclosure.
Figure 12:
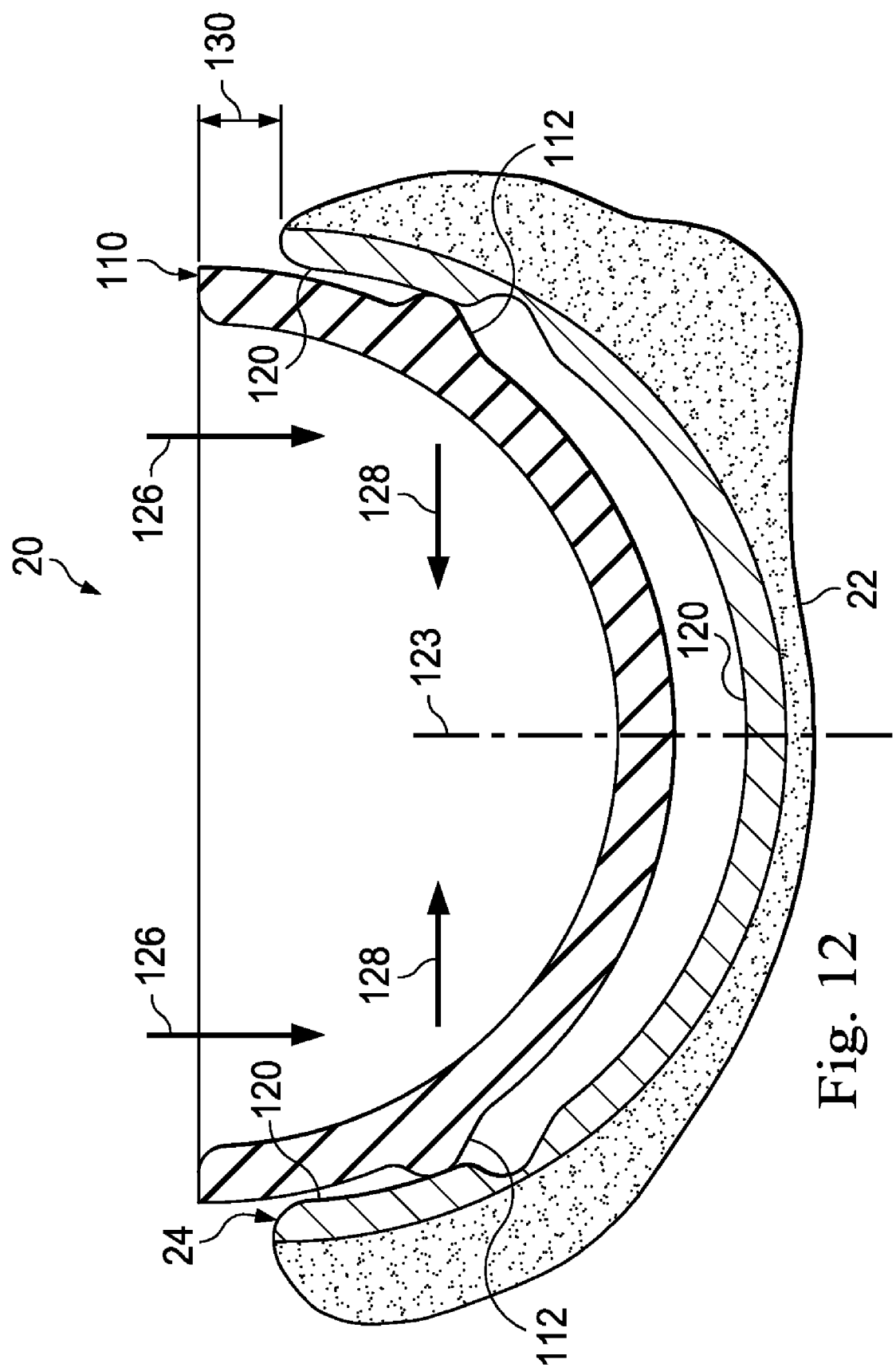
FIG. 12 is a diagrammatic cross-sectional view of a stage of the prosthetic device being implanted into the prepared articular cartilage of the natural acetabulum similar to that of FIG. 11, but showing a subsequent stage of implantation.
Figure 13:
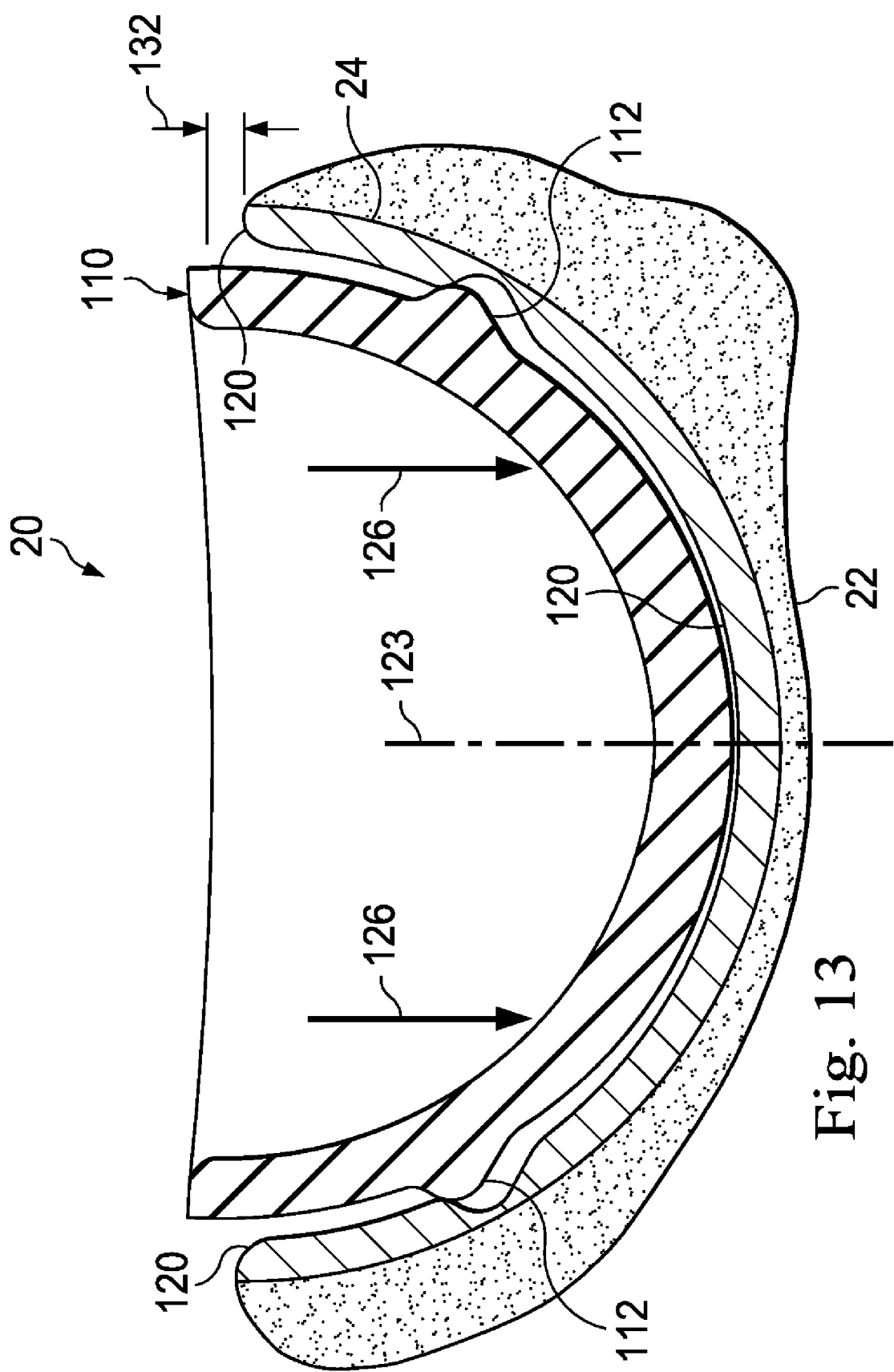
FIG. 13 is a diagrammatic cross-sectional view of a stage of the prosthetic device being implanted into the prepared articular cartilage of the natural acetabulum similar to that of FIGS. 11 and 12, but showing a subsequent stage of implantation.
Figure 14:
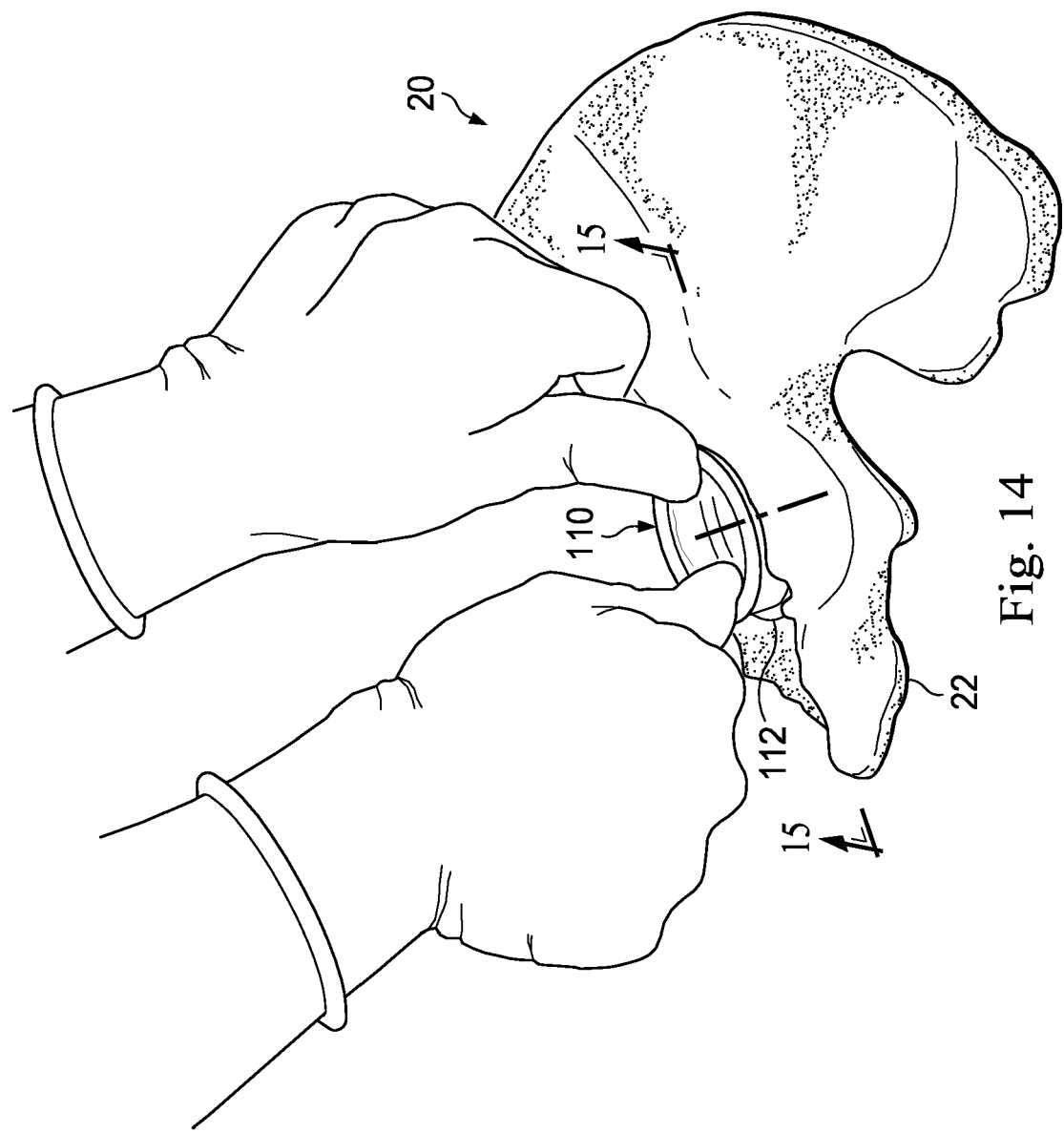
FIG. 14 is a diagrammatic perspective view of a step of securely implanting a prosthetic device into the prepared articular cartilage of a natural acetabulum similar to that of FIG. 10, but showing a subsequent step.
Figure 15:
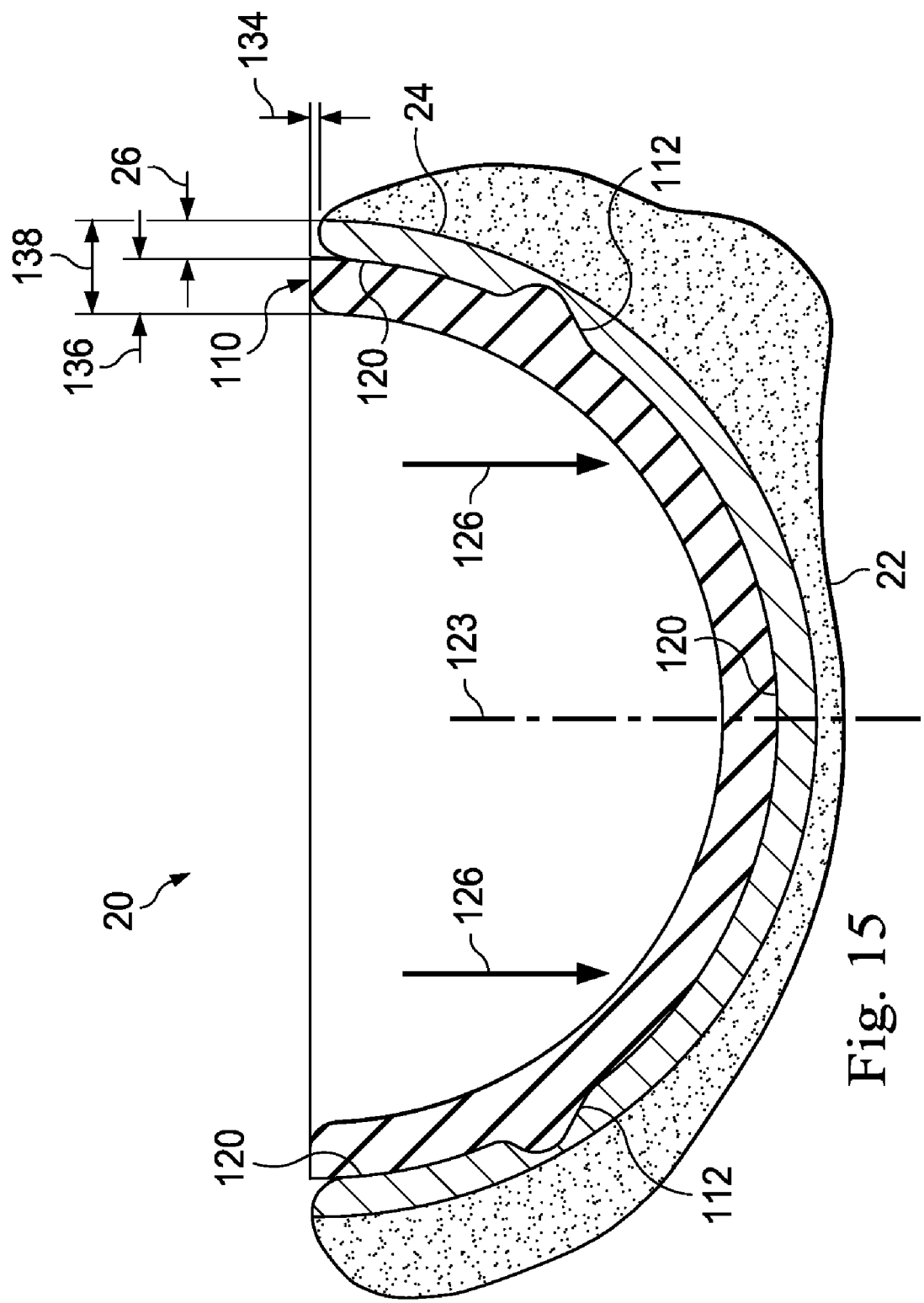
FIG. 15 is a diagrammatic cross-sectional view of a stage of the prosthetic device being implanted into the prepared articular cartilage of the natural acetabulum similar to that of FIGS. 11, 12, and 13, but showing the device fully implanted into the prepared articular cartilage.

Reference is now made to FIGS. 10-15, which illustrate the completion of the snap-fit engagement of the prosthetic acetabular socket 110 with the prepared acetabulum 20 according to one embodiment of the present disclosure. Specifically, FIG. 10 is a diagrammatic perspective view of a step of securely implanting the prosthetic acetabular socket 110 into the prepared articular cartilage 24 of the natural acetabulum 20; FIG. 11 is a diagrammatic cross-sectional view of a stage of the prosthetic acetabular socket 110 being implanted into the prepared articular cartilage 24; FIG. 12 is a diagrammatic cross-sectional view of a stage of the prosthetic acetabular socket 110 being implanted into the prepared articular cartilage 24 similar to that of FIG. 11, but showing a subsequent stage of implantation; FIG. 13 is a diagrammatic cross-sectional view of a stage of the prosthetic acetabular socket 110 being implanted into the prepared articular cartilage 24 similar to that of FIGS. 11 and 12, but showing a subsequent stage of implantation; FIG. 14 is a diagrammatic perspective view of a step of securely implanting a prosthetic acetabular socket 110 into the prepared articular cartilage 24 similar to that of FIG. 10, but showing a subsequent step; and FIG. 15 is a diagrammatic cross-sectional view of a stage of the prosthetic acetabular socket 110 being implanted into the prepared articular cartilage 24 similar to that of FIGS. 11, 12, and 13, but showing the device fully implanted into the prepared articular cartilage.

Referring more specifically to FIG. 10, following introduction and placement of the implantable artificial acetabular socket 110 adjacent the prepared acetabulum 20, a surgeon, using his fingers, gently begins urging the artificial acetabular socket 110 into position for snap-fit engagement with the articular cartilage 24. This position is shown clearly in the cross-sectional view of FIG. 11, which is a cross-sectional illustration of the orientation of FIG. 10. Accordingly, referring more specifically to FIG. 11, the annular snap-fit protrusion 112 lies in touching, generally non-compressive engagement with an outer portion of a concave surface 120 of the articular cartilage 24. The outer portion of the concave surface 120 lies above the recess 122 formed in the articular cartilage 24 during preparation of the acetabulum 20. In the present embodiment, the recess 122 is generally annular extending around the concave surface 120. As described above, the recess 122 is sized, shaped, and positioned for snap-fit engagement with the annular protrusion 112 of the prosthetic acetabular socket 110. Accordingly, initial engagement of the protrusion 112 with the outer portion of the concave surface 120 causes the implantable artificial acetabular socket 110 to rest at a position such that the rim or outer edge of the socket 110 lies above a corresponding outer edge of prepared acetabulum 20. The separation between the outer edges of the implantable artificial acetabular socket 110 and the acetabulum 20, along axis 123, is indicated by distance 124.

Referring more specifically to FIG. 12, the prosthetic acetabular socket 110 has been further urged towards snap-fit engagement with the articular cartilage 24. The surgeon or other medical professional uses his fingers to gently engage the inner concave surface of the artificial acetabular socket 110 and presses thereon in a direction indicated by arrows 126, which direction lies generally along axis 123. The application of this pressure causes displacement of artificial acetabular socket 110 in the direction 126. Due to the concave configuration of the outer portion of concave surface 120, this displacement produces radially inward compression of artificial acetabular socket 110 at annular protrusion 112, as indicated by arrows 128. This radially inward compression results in deformation of the artificial acetabular socket 110 at annular protrusion 112 and in the general region thereof. Naturally, displacement of artificial acetabular socket 110 in direction 126 reduces the separation between the outer edges of the implantable artificial acetabular socket 110 and the acetabulum 20, as indicated by distance 130 which is less than distance 124 of FIG. 10.

Referring more specifically to FIG. 13, the prosthetic acetabular socket 110 has been further urged towards snap-fit engagement with the articular cartilage 24. The surgeon or other medical professional uses his fingers to gently engage the inner concave surface of the artificial acetabular socket 110 and further presses thereon in a direction indicated by arrows 126, which direction lies generally along axis 123. The application of this pressure causes displacement of artificial acetabular socket 110 in the direction 126. This further displacement produces sliding pressure engagement between underlying surface portion of the annular protrusion 112 and the concave surface 120 until the protrusion 112 reaches the recess 122. It is noted that the resiliency of the artificial acetabular socket 110 causes radially outward displacement of protrusion 112 once the protrusion reaches the recess 122 Again, this further displacement of artificial acetabular socket 110 in direction 126 further reduces the separation between the outer edges of implantable artificial acetabular socket 110 and the acetabulum 20 as indicated by distance 132, which is less than the distances 130 and 124 of FIGS. 11 and 10 respectively. Further, as shown engagement of the protrusion 112 with the concave surface 120 causes the prosthetic device 110 to deform. Specifically, the prosthetic device 110, including its outer and inner surfaces are deformed inwardly such that the outer and inner surface are not substantially, partially spherical. Instead, the outer and inner surfaces become partially elliptical or oblonged. Thus, as shown the bottom portion of the outer surface as viewed in FIG. 13 is closer to the concave surface 120 than the side portions of the outer surface.

Referring now to FIGS. 14 and 15, the prosthetic acetabular socket 110 is urged into complete snap-fit engagement with the articular cartilage 24. The surgeon, using his fingers, presses on the artificial acetabular socket 110 in direction 126. In some instances the surgeon presses on the rim of the socket 110 at this stage to urged the socket into complete engagement with the acetabulum 20. As seen in FIG. 15, the application of this further pressure causes further displacement of artificial acetabular socket 110 in direction 126. This further displacement produces the resultant sliding snap-fit engagement between protrusion 112 and recess 122. It is appreciated that the snap-fit engagement of the artificial acetabular socket 110 with the prepared articular cartilage 24 produces locking of the artificial acetabular socket 110 relative to the acetabulum 20 without damaging the underlying bone structure of the acetabulum. As shown, even in full snap-fit engagement the outer edge of the socket 110 may extend beyond the outer edge of the acetabulum, as indicated by distance 134, in some embodiments. In other embodiments, however, the outer edge of the socket 110 is substantially aligned with or below the outer edge of the acetabulum.

As shown, in the present embodiment the acetabular socket 110 generally has a width or thickness 136 (excluding protrusion 112). The thickness 136 is generally between about 0.5 mm and about 6.0 mm. As described above the articular cartilage 24 has a thickness 26, which is generally less than about 4.0 mm. Accordingly, the thickness 136 of the socket 110 may be less than, equal to, or greater than the thickness 26 of the articular cartilage 24. Together the articular cartilage 24 and the acetabular socket 110 extend from the bone 22 of the acetabulum 20 a distance 138. Generally, the distance 138 is between about 2.0 mm and about 10.0 mm. In some instances, the specific combined thickness is determined based on a femoral head (natural or artificial) that is to be mated with the socket 110. Further, the projections and/or recesses of the prosthetic devices and the projections and/or recesses formed in the articular cartilage generally have thickness between about 0.5 mm and about 2.5 mm. Accordingly, the individual thicknesses of the prosthetic device and the prepared articular cartilage may vary up to 2.5 mm, while the combined thickness remains substantially constant. In one embodiment, the thickness 26 of the articular cartilage 26 is approximately 3.0 mm, the thickness 136 of the socket 110 is approximately 4.0 mm, and the protrusion 112 and recess 122 have a respective height and depth of approximately 2.0 mm.

Figure 16:
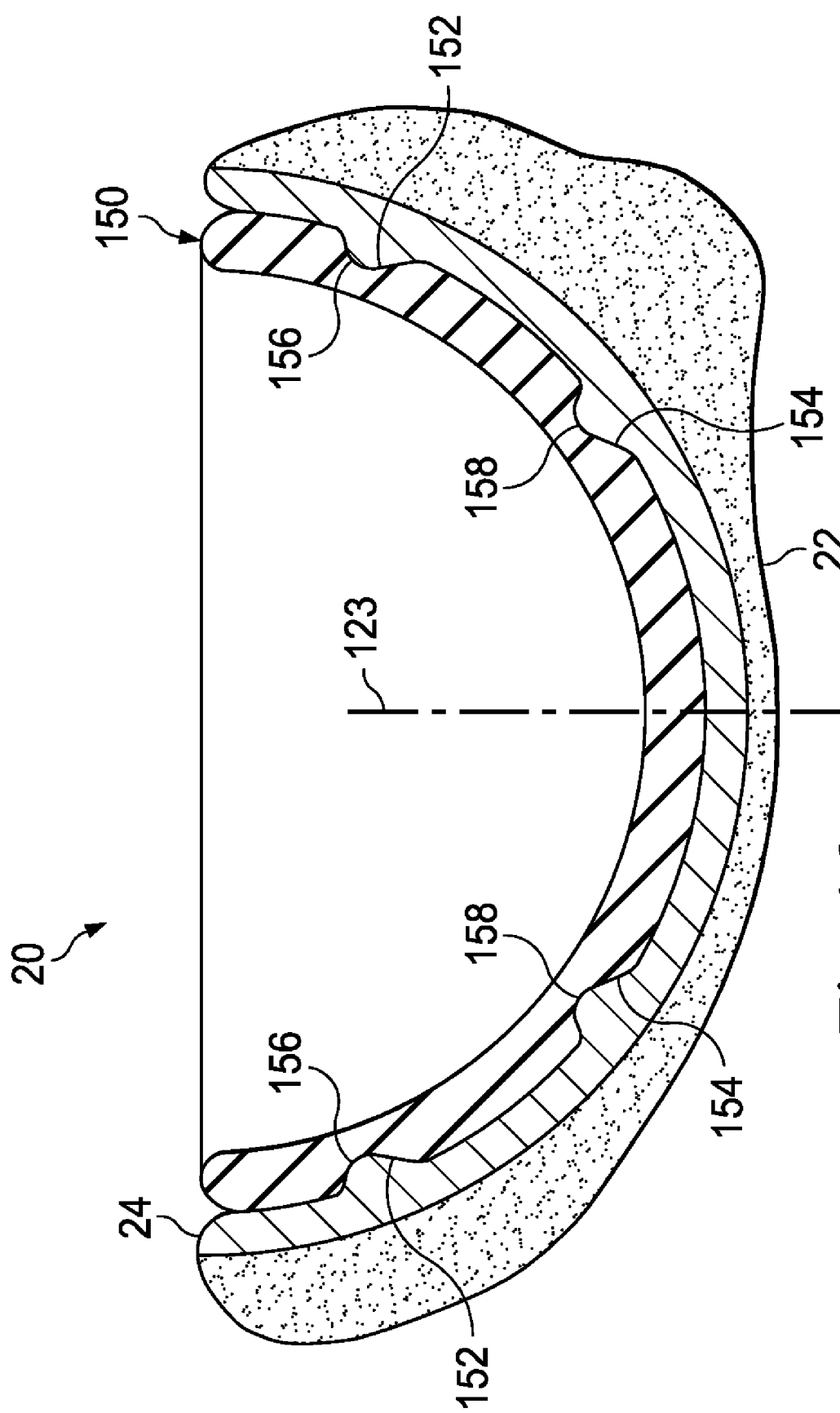
FIG. 16 is a diagrammatic cross-sectional view of a prosthetic device fully implanted into prepared articular cartilage of the natural acetabulum similar to that of FIG. 15, but showing an alternative embodiment of the present disclosure.

Referring to FIG. 16, shown therein is a diagrammatic cross-sectional view of a prosthetic device 150 fully implanted into prepared articular cartilage 24 of the natural acetabulum 20 similar to that of FIG. 15, but showing an alternative embodiment of the present disclosure. In particular, the prosthetic device 150 includes a pair of annular recesses formed therein 152, 154. The annular recesses 152, 154 may be continuous about the circumference of the device 150 or defined by a plurality of discrete recess portions. As shown, the recesses 152, 154 are spaced from one another between the apex of the device 150 and the rim of the device. In the illustrated embodiment, the articular cartilage 24 has been prepared to form a pair of annular protrusions 156, 158 extending therefrom. In that regard, the protrusions 156, 158 are sized and shaped for snap-fit engagement with the annular recesses 152, 154 of the device 150. Accordingly, the protrusions 156, 158 may also be continuous or discrete. While the device 150 and cartilage 24 are shown as having 2 recesses and protrusions, respectively, in other embodiments they may include additional recesses and protrusions. In that regard, in some embodiments a plurality of interlocking recesses and protrusions are utilized to secure the device 150 to the cartilage 24. In some instances, using a plurality of recesses and protrusions allows for the depth of the recesses and height of the protrusions to be less, such that the prosthetic device can be used with a patient with minimal healthy articular cartilage. In some instances, a patient with at least 0.5 mm of healthy articular cartilage can receive a prosthetic device having a plurality of projections and/or recesses in accordance with the present disclosure.

While the device 150 is shown as having the recesses 152, 154 and the cartilage 24 is shown as having the protrusions 156, 158, in other embodiments the device 150 includes protrusions and the cartilage 24 is prepared to include recesses. Similarly, each of the device 150 and the cartilage 24 may include both at least one projection and at least one recess in some instances. In the present embodiment, the device 150 includes a rounded outer rim or edge as shown. In some embodiments, a protrusion at least partially matching that curvature of the outer rim is formed in the articular cartilage to further secure the device in place. In other embodiments, the articular cartilage is also rounded as shown in FIG. 16. In other instances, the device 150 includes substantially as seen in other embodiments of the present disclosure. Similarly, in some instances the other may include a rounded outer rim or edge as shown in FIG. 16.

In addition to or in lieu of the snap-fit engagement features, the engagement surface of the prosthetic devices may be treated to enhance engagement between the articular cartilage and the device. In some instances, the engagement surface of the device is roughened to increase the friction between the articular cartilage and the device. In that regard, the friction between the articular cartilage and the prosthetic device is greater than the friction between the prosthetic device and the femoral head (artificial or natural) received by the prosthetic device, such that articulation of the femoral head with respect to the device does impart movement upon the prosthetic device relative to the articular cartilage. Further, the engagement surface may be treated with biologics to encourage ingrowth of articular cartilage. In some instances, the engagement surface receives one or more surface treatments as described in U.S. patent application Ser. No. 10/497,897 titled "CUSHION BEARING IMPLANTS FOR LOAD BEARING APPLICATIONS," hereby incorporated by reference in its entirety.

Figure 17:
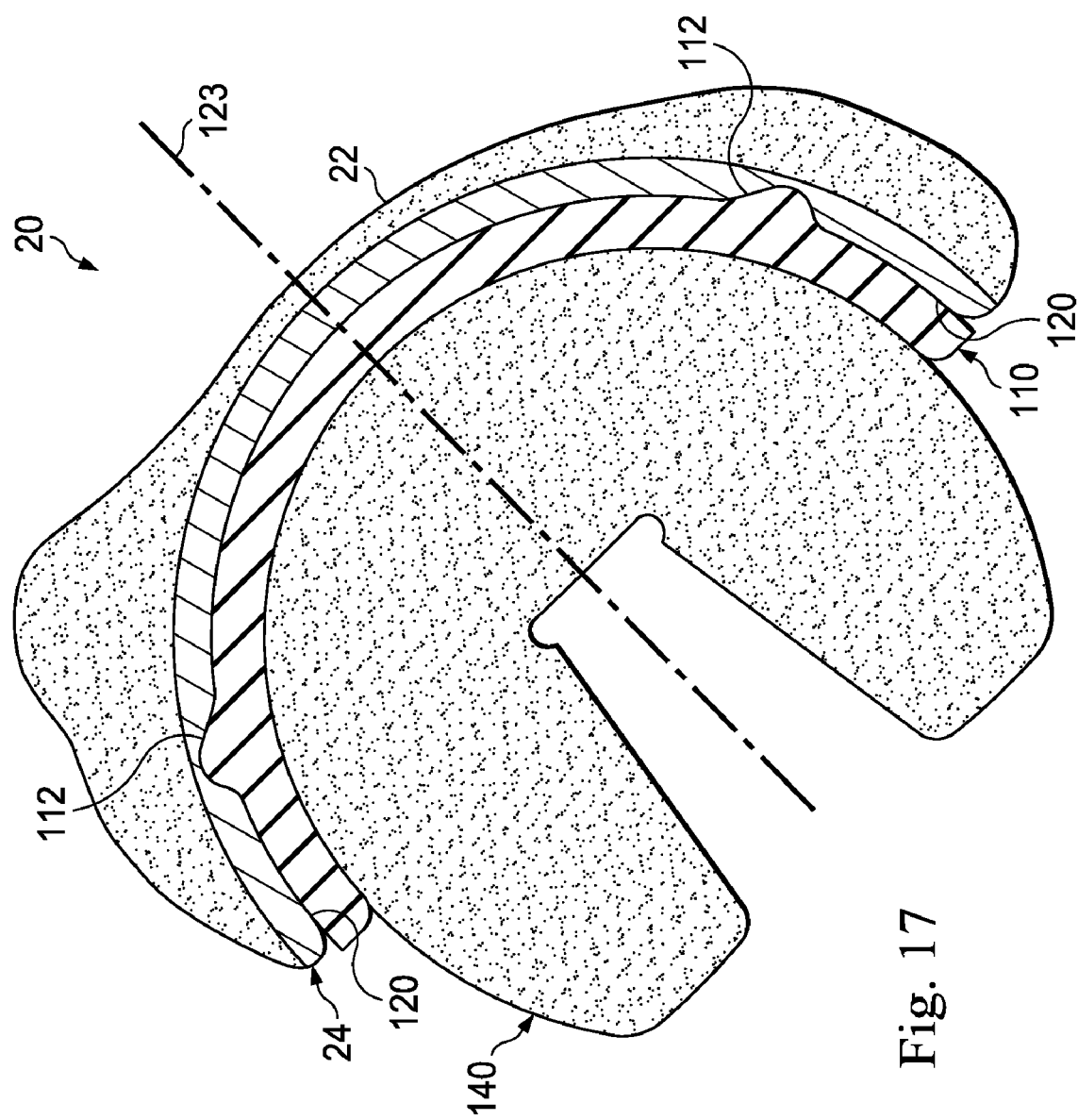
FIG. 17 is a diagrammatic cross-sectional view of a prosthetic device fully implanted into the prepared articular cartilage of a natural acetabulum and engaged with a femoral head according to one embodiment of the present disclosure.

Finally, referring to FIG. 17, a femoral head 140 is mated with a prosthetic device—the acetabular socket 110 is illustrated—that has been fully implanted into the prepared acetabulum. The femoral head may be either a natural or artificial femoral head. In the case of a natural femoral head, the bone may be prepared to include a radius of curvature substantially matching that of the inner articulating surface of the prosthetic device.

In some embodiments, the at least the outer surface of the prosthetic device is wetted prior to implantation into the prepared acetabulum. In other instances, the prosthetic device is saturated prior to implantation into the prepared acetabulum. In some instances, the prosthetic device is made of a water-absorbent polymer that is hydrated prior to implantation. Wetting and/or saturating the prosthetic device prior to implantation can both lubricate the device making it easier to insert as well as increase the locking engagement of the prosthetic device with the articular cartilage once the device is seated within the articular cartilage by creating a fluid adhesion bond or fluid lock between the articular cartilage and the prosthetic device. In some instances, the fluid adhesion bond between the articular cartilage and the prosthetic device is sufficient to prevent unwanted disengagement of the device from the acetabulum in a direction opposite insertion direction 126, as shown in FIGS. 12 and 13 for example. In that regard, the fluid adhesion bond does not necessarily prevent rotational movement of the device relative to the articular cartilage, but instead prevents unwanted separation of the device from the prepared articular cartilage. In some embodiments, the fluid adhesion bond is combined with the snap-fit interface described above to increase the engagement. In one such embodiment, the snap-fit interface is configured to prevent unwanted rotation of the prosthetic device relative to the articular cartilage, while the fluid adhesion bond prevents axial displacement of the prosthetic device relative to the acetabulum. The fluid used to wet or saturate the device may be saline solution or other suitable biocompatible liquid for creating the fluid lock.

Referring again to FIG. 15, as seen therein a layer of fluid 186 is positioned between the prosthetic acetabular cup 110 and the articular cartilage 24 and creates a liquid adhesion bond therebetween. In some instances creation of the liquid adhesion bond is dependent on the surface of the device substantially matching the geometry of the prepared surface of the articular cartilage. Accordingly, in some embodiments, the deformation of the outer portion or surface of the device over time or "creep" of the device causes the outer surface of the device to better match the articular cartilage over time. Accordingly, in some instances, the device is not subjected to a liquid adhesion bond immediately upon implantation but obtains a liquid adhesion bond over time. In some instances, synovial fluid of the hip joint is introduced and/or migrates between the device and the articular cartilage over time to create and/or enhance the fluid adhesion bond.

In some instances, the prosthetic devices of the present disclosure are fiber reinforced, include a deformation control element, or comprise a material or combination of materials particularly suited for positioning within an articulating joint. In some embodiments, the prosthetic devices are formed of materials or combinations of materials as described in U.S. patent application Ser. No. 10/497,897 titled "CUSHION BEARING IMPLANTS FOR LOAD BEARING APPLICATIONS" and U.S. patent application Ser. No. 12/100,090 titled "MANUFACTURING AND MATERIAL PROCESSING FOR PROSTHETIC DEVICES", each hereby incorporated by reference in its entirety.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure. Also, it will be fully appreciated that variations of the above-disclosed and other features and functions, or alternatives thereof, may be combined into other methods, systems, apparatus, or applications. Similarly, various presently unforeseen or unanticipated alternatives, modifications, and/or variations of the present disclosure subsequently made by those skilled in the art are also encompassed by the present disclosure and the following claims.

The invention claimed is:

1. A method of implanting a prosthetic acetabular cup into a patient, comprising:
    gaining access to an acetabulum of the patient, the acetabulum comprising an inner portion formed of bone and an outer portion formed of articular cartilage;
    creating a first engagement feature within the articular cartilage of the outer portion of the acetabulum without removing any portion of bone from the inner portion of the acetabulum, the first engagement feature sized, shaped, and positioned to mate with a second engagement feature of the prosthetic acetabular cup; and
    securely anchoring the prosthetic acetabular cup with the acetabulum by engaging the second engagement feature of the prosthetic acetabular cup with the first engagement feature in the articular cartilage of the outer portion of the acetabulum.

2. The method of claim 1, wherein creating the first engagement feature comprises creating a recess in the articular cartilage.

3. The method of claim 2, wherein creating the recess comprises forming an annular recess in the articular cartilage with a depth between about 0.5 mm and about 2.0 mm.

4. The method of claim 2, wherein securely anchoring the prosthetic acetabular cup comprises engaging the second engagement feature of the prosthetic acetabular cup with the recess in the articular cartilage, where the second engagement feature comprises a projection extending from an outer surface of the prosthetic acetabular cup.

5. The method of claim 3, wherein creating the first engagement feature comprises forming a projection in the articular cartilage.

6. The method of claim 1, wherein securely anchoring the prosthetic acetabular cup further comprises creating a liquid adhesion bond between the prosthetic acetabular cup and the articular cartilage of the outer portion of the acetabulum.

7. The method of claim 6, wherein creating the adhesion bond comprises wetting an outer surface of the prosthetic acetabular cup prior to snap-fitting the snap-fit structure of the prosthetic acetabular cup into the recess.

8. The method of claim 1, wherein creating the first engagement feature comprises forming a plurality of recesses in the articular cartilage.

9. The method of claim 8, wherein the plurality of recesses are substantially aligned to form an annular array of recesses in the articular cartilage.

10. The method of claim 8, wherein each of the plurality of recesses comprises an annular recess in the articular cartilage, each of the plurality of recesses being spaced from one another.

11. A method of implanting a polycarbonate polyurethane prosthetic acetabulum into a hip joint of a patient, comprising:
gaining access to a natural acetabulum of the patient, the natural acetabulum comprising a first outer portion for articulating engagement with a femoral head of the patient, the first outer portion formed of articular cartilage, the natural acetabulum further comprising a second inner portion adjacent the first outer portion, the second inner portion formed of bone;
removing a portion of the articular cartilage of the first outer portion without damaging any bone of the second inner portion to create at least one first anchoring structure within the articular cartilage, the at least one first anchoring structure shaped to mate with at least one second anchoring structure of the prosthetic acetabulum; and
engaging the prosthetic acetabulum with the first outer portion of the acetabulum such that an outer engagement surface of the prosthetic acetabulum engages the first outer portion of the acetabulum via a liquid adhesion bond and the at least one second anchoring structure of the prosthetic acetabulum engages the at least one first anchoring structure in the articular cartilage, wherein the engagement of the at least second anchoring structure of the prosthetic acetabulum prevents unwanted rotation of the prosthetic acetabulum relative to the first outer portion of the natural acetabulum and the liquid adhesion between the prosthetic acetabulum and the first outer portion prevents unwanted separation of the prosthetic acetabulum from the first outer portion.

12. The method of claim 11, wherein removing the portion of the articular cartilage comprises creating an annular recess in the articular cartilage.

13. The method of claim 11, wherein removing the portion of the articular cartilage comprises removing between about 0.5 mm and about 2.0 mm of articular cartilage depth.

14. The method of claim 11, wherein removing the portion of the articular cartilage comprises engaging an anchoring portion of a tool with a portion of the natural acetabulum and rotating a cutting portion of the tool about a longitudinal axis of the tool relative to the anchoring portion to form the at least one recess in the articular cartilage.

15. The method of claim 14, wherein engaging the anchoring portion of the tool with the portion of the natural acetabulum comprises engaging the anchoring portion with a bony portion of the hip joint.

16. The method of claim 14, wherein engaging the anchoring portion of the tool with the portion of the natural acetabulum comprises engaging the anchoring portion with the articular cartilage of the first outer portion without damaging the articular cartilage.

17. The method of claim 16, further comprising wetting the outer engagement surface of the prosthetic acetabulum with a liquid configured for creating the liquid adhesion bond prior to engaging the prosthetic acetabulum with the first outer portion of the natural acetabulum.

18. The method of claim 17, further comprising saturating the prosthetic acetabulum with the liquid configured for creating the liquid adhesion bond prior to engaging the prosthetic acetabulum with the first outer portion of the natural acetabulum.

19. A method of implanting a flexible prosthetic acetabular cup into a patient, comprising:
gaining access to the acetabulum of the patient, the acetabulum comprising an inner portion formed of bone and an outer portion formed of articular cartilage;
determining whether the articular cartilage of the outer portion is suitable for receiving the flexible prosthetic acetabular cup;
engaging an anchoring portion of a tool with the articular cartilage and rotating a cutting portion of the tool about a longitudinal axis of the tool relative to the anchoring portion to form a recess in the articular cartilage without removing any portion of the bone from the inner portion of the acetabulum, the recess shaped to mate with an engagement structure of the flexible prosthetic acetabular cup and having a depth between about 0.5 mm and about 2.0 mm; and
securing the flexible prosthetic acetabular cup to the articular cartilage, including positioning the engagement structure of the flexible prosthetic acetabular cup into the recess in the articular cartilage of the outer portion of the acetabulum.

20. The method of claim 19, wherein determining whether the articular cartilage of the outer portion is suitable for receiving the flexible prosthetic acetabular cup comprises imaging the patient's hip joint to determine a thickness of the articular cartilage, wherein the thickness must be at least 2 mm for the articular cartilage to be considered suitable.

* * * * *